(12) United States Patent
Wang et al.

(10) Patent No.: US 9,237,865 B2
(45) Date of Patent: Jan. 19, 2016

(54) ANALYTE SENSORS AND METHODS FOR MAKING AND USING THEM

(75) Inventors: Yunbing Wang, Sunnyvale, CA (US); Udo Hoss, Sherman Oaks, CA (US); Rajiv Shah, Rancho Palos Verdes, CA (US); Jenn-Hann Larry Wang, Northridge, CA (US); William P. Van Antwerp, Valencia, CA (US); Brooks B. Cochran, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1395 days.

(21) Appl. No.: 11/492,273

(22) Filed: Jul. 25, 2006
(Under 37 CFR 1.47)

(65) Prior Publication Data

US 2008/0026473 A1   Jan. 31, 2008

(51) Int. Cl.
| | |
|---|---|
| *G01N 33/48* | (2006.01) |
| *A61B 5/05* | (2006.01) |
| *A61B 5/1486* | (2006.01) |
| *A61B 5/145* | (2006.01) |
| *C12Q 1/00* | (2006.01) |

(52) U.S. Cl.
CPC ......... *A61B 5/14865* (2013.01); *A61B 5/14532* (2013.01); *A61B 5/14546* (2013.01); *C12Q 1/006* (2013.01); *Y10T 29/49002* (2015.01)

(58) Field of Classification Search
USPC ..................................... 600/345, 347; 436/63
See application file for complete search history.

(56) References Cited

U.S. PATENT DOCUMENTS

| | | | |
|---|---|---|---|
| 2,402,950 | A | 7/1946 | Culver et al. |
| 2,519,541 | A | 8/1950 | Bryant |
| 2,899,658 | A | 8/1959 | Bean, Jr. |
| 4,034,959 | A | 7/1977 | Morrison |
| 4,104,099 | A | 8/1978 | Scherrer |
| 4,136,250 | A * | 1/1979 | Mueller et al. ................ 528/29 |
| 4,163,544 | A | 8/1979 | Fowler et al. |
| 4,356,074 | A | 10/1982 | Johnson |
| 4,373,009 | A | 2/1983 | Winn |
| 4,373,527 | A | 2/1983 | Fischell |
| 4,484,987 | A | 11/1984 | Gough |
| 4,560,375 | A | 12/1985 | Schulte et al. |

(Continued)

FOREIGN PATENT DOCUMENTS

| | | |
|---|---|---|
| EP | 0 747 069 A2 | 12/1996 |
| EP | 0 826 382 A2 | 3/1998 |

(Continued)

OTHER PUBLICATIONS

Stumbe J-F, et al., "Synthesis of poly(methyl methacrylate)-g-poly(dimethyl siloxane) graft copolymers via a miniemulsion process", Polymer Bulletin 47, 277-282 (2001) (Stumbe).*

(Continued)

*Primary Examiner* — Michael Kahelin
*Assistant Examiner* — Mitchell E Alter
(74) *Attorney, Agent, or Firm* — Gates & Cooper LLP

(57) ABSTRACT

Embodiments of the invention provide analyte sensors having elements designed to modulate their chemical reactions as well as methods for making and using such sensors. In certain embodiments of the invention, the sensor includes a hydrophilic comb-copolymer having a central chain and a plurality of side chains coupled to the central chain, wherein at least one side chain comprises a silicone moiety.

7 Claims, 10 Drawing Sheets

(56) References Cited

U.S. PATENT DOCUMENTS

| | | | |
|---|---|---|---|
| 4,568,250 A | 2/1986 | Falk et al. | |
| 4,569,641 A | 2/1986 | Falk et al. | |
| 4,573,994 A | 3/1986 | Fischell et al. | |
| 4,626,244 A | 12/1986 | Reinicke | |
| 4,636,150 A | 1/1987 | Falk et al. | |
| 4,654,006 A | 3/1987 | Kusano et al. | |
| 4,714,234 A | 12/1987 | Falk et al. | |
| 4,759,828 A | 7/1988 | Young et al. | |
| 4,769,013 A | 9/1988 | Lorenz et al. | |
| 4,783,441 A | 11/1988 | Thurow | |
| 4,890,620 A | 1/1990 | Gough | |
| 4,897,173 A | 1/1990 | Nankai et al. | |
| 4,950,256 A | 8/1990 | Luther et al. | |
| 4,958,661 A | 9/1990 | Holtermann et al. | |
| 5,001,009 A | 3/1991 | Whitbourne | |
| 5,019,260 A | 5/1991 | Gsell et al. | |
| 5,077,210 A | 12/1991 | Eigler et al. | |
| 5,108,819 A | 4/1992 | Heller et al. | |
| 5,128,170 A | 7/1992 | Matsuda et al. | |
| 5,165,407 A | 11/1992 | Wilson et al. | |
| 5,178,366 A | 1/1993 | Kojima et al. | |
| 5,183,472 A | 2/1993 | Jaehrling et al. | |
| 5,196,088 A | 3/1993 | Soda | |
| 5,200,051 A | 4/1993 | Cozzette et al. | |
| 5,212,050 A | 5/1993 | Mier et al. | |
| 5,229,172 A | 7/1993 | Cahalan et al. | |
| 5,281,324 A | 1/1994 | Kiesele et al. | |
| 5,288,636 A | 2/1994 | Pollmann et al. | |
| 5,299,571 A | 4/1994 | Mastrototaro | |
| 5,322,063 A | 6/1994 | Allen et al. | |
| 5,328,954 A | 7/1994 | Sarangapani | |
| 5,330,911 A | 7/1994 | Hubbell et al. | |
| 5,331,027 A | 7/1994 | Whitbourne | |
| 5,390,671 A | 2/1995 | Lord et al. | |
| 5,390,691 A | 2/1995 | Sproule | |
| 5,391,250 A | 2/1995 | Cheney, II et al. | |
| 5,411,647 A | 5/1995 | Johnson et al. | |
| 5,415,938 A | 5/1995 | Cahalan et al. | |
| 5,433,710 A | 7/1995 | Van Antwerp et al. | |
| 5,482,473 A | 1/1996 | Lord et al. | |
| 5,568,806 A | 10/1996 | Cheney, II et al. | |
| 5,607,475 A | 3/1997 | Cahalan et al. | |
| 5,609,629 A | 3/1997 | Fearnot et al. | |
| 5,620,738 A | 4/1997 | Fan et al. | |
| 5,643,681 A | 7/1997 | Voorhees et al. | |
| 5,648,442 A | 7/1997 | Bowers et al. | |
| 5,662,960 A | 9/1997 | Hostettler et al. | |
| 5,672,638 A | 9/1997 | Verhoeven et al. | |
| 5,679,615 A * | 10/1997 | Matsumoto et al. | 503/217 |
| 5,696,314 A * | 12/1997 | McCaffrey et al. | 205/778 |
| 5,702,754 A | 12/1997 | Zhong | |
| 5,702,818 A | 12/1997 | Cahalan et al. | |
| 5,711,959 A | 1/1998 | Kohler et al. | |
| 5,777,060 A * | 7/1998 | Van Antwerp | 528/28 |
| 5,786,439 A | 7/1998 | Van Antwerp et al. | |
| 5,804,048 A | 9/1998 | Wong et al. | |
| 5,809,242 A | 9/1998 | Shaw et al. | |
| 5,858,186 A | 1/1999 | Glass | |
| 5,913,040 A | 6/1999 | Rakavy et al. | |
| 5,939,208 A | 8/1999 | Stoy | |
| 5,964,993 A | 10/1999 | Blubaugh, Jr. et al. | |
| 5,986,015 A * | 11/1999 | Midha et al. | 525/370 |
| 6,011,537 A | 1/2000 | Slotznick | |
| 6,013,855 A | 1/2000 | McPherson et al. | |
| 6,030,827 A * | 2/2000 | Davis et al. | 435/287.1 |
| 6,103,033 A | 8/2000 | Say et al. | |
| 6,106,820 A * | 8/2000 | Morrissey et al. | 424/78.18 |
| 6,162,611 A | 12/2000 | Heller et al. | |
| 6,340,421 B1 | 1/2002 | Vachon et al. | |
| 6,368,274 B1 | 4/2002 | Van Antwerp et al. | |
| 6,411,998 B1 | 6/2002 | Bryant et al. | |
| 6,413,393 B1 | 7/2002 | Van Antwerp et al. | |
| 6,497,729 B1 | 12/2002 | Moussy et al. | |
| 6,551,276 B1 | 4/2003 | Mann et al. | |
| 6,558,351 B1 | 5/2003 | Steil et al. | |
| 6,741,877 B1 | 5/2004 | Shults et al. | |
| 7,613,491 B2 * | 11/2009 | Boock et al. | 600/347 |
| 2003/0069383 A1 * | 4/2003 | Van Antwerp et al. | 528/77 |
| 2003/0100040 A1 | 5/2003 | Bonnecaze et al. | |
| 2004/0008956 A1 | 1/2004 | Frohne et al. | |
| 2004/0009161 A1 | 1/2004 | Escary | |
| 2004/0074785 A1 * | 4/2004 | Holker et al. | 205/777.5 |
| 2005/0090607 A1 * | 4/2005 | Tapsak et al. | 524/588 |
| 2005/0272989 A1 * | 12/2005 | Shah et al. | 600/345 |
| 2006/0052745 A1 | 3/2006 | Van Antwerp et al. | |
| 2006/0258761 A1 * | 11/2006 | Boock et al. | 521/50 |

FOREIGN PATENT DOCUMENTS

| | | |
|---|---|---|
| JP | 60173452 | 9/1985 |
| JP | 11503772 | 3/1999 |
| JP | 2005320521 | 11/2005 |
| JP | 2009544407 | 12/2009 |
| WO | 9315651 | 8/1993 |
| WO | WO 98/07458 | 2/1998 |
| WO | WO 98/08553 | 3/1998 |
| WO | WO 98/10805 | 3/1998 |
| WO | WO 98/19627 | 5/1998 |
| WO | WO 98/56293 | 12/1998 |
| WO | WO 99/21703 | 5/1999 |
| WO | WO 99/22993 | 5/1999 |
| WO | WO 99/45375 | 9/1999 |
| WO | WO 99/45387 | 9/1999 |
| WO | WO 99/56613 | 11/1999 |
| WO | WO 01/58348 | 8/2001 |
| WO | WO02/053764 | 7/2002 |
| WO | 2005/121355 | 12/2005 |
| WO | WO2006/127694 | 11/2006 |
| WO | 2009032588 | 3/2009 |
| WO | 2009121026 | 10/2009 |

OTHER PUBLICATIONS

European Search Report dated Jan. 18, 2008.

"Flexible circuits at Extreme Density", 8 unnumbered pages of various dates (Metrigraphics, Wilmington, MA).

Kimura, J. et al., 1989, "Evaluation of an Albumin-Based, Spin-Coated, Enzyme-Immobilized Membrane for an Isfet Glucose Sensor by Computer Simulation," Journal of Membrane Science, 43:291-305.

Koudelka, M., et al., "Planar Amperometric Enzyme-Based Glucose Microelectrode," Sensors and Actuators, 18 (Elsevier Sequoia, The Netherlands—1989), pp. 157-165.

Koudelka, M., et al., "In-vivo Behaviour of Hypodermically Implanted Microfabricated Glucose Sensors," *Biosensors & Bioelectrics* 6, (Elsevier Science Publishers Ltd., England—1991) pp. 31-36.

Mastrototaro, John J., et al., "An electroenzymatic glucose sensor fabricated on a flexible substrate," *Sensors and Actuators B.5* (Elsevier Sequoia 1991), p. 139-144.

"Metrigraphics Ion Beam Etching Capability," 1 page, no date (Metrigraphics, Wilmington, MA).

"3M Specifications and Design Guidelines, Microflex Circuits for IC Interconnect Solutions," pp. 1-32 (the entire document), 1997 (3M Electronic Products Division, Austin, TX).

"3M Offers More Solutions for the Semiconductor Industry", the entire document, 1997 (3M Electronic Products Division, Austin, TX).

"Microflex Solutions from 3M," the entire document, 1996 (3M Electronic Products Division, Austin, TX).

"5 Micron Wide Conductors and Spaces on . . . PZT, Alumina, Glass and Flexible Materials," 1 page, no date (Metrigraphics, Wilmington, MA).

Thurow et al., "Stabilisation of Dissolved Proteins Against Denaturation at Hydrophobic Interfaces," Diabetologia, 1984, 27: 212-218.

Urban, G., et al., "Miniaturized multi-enzyme biosensors integrated with pH sensors on flexible polymer carriers for in vivo applications," *Biosensors & Bioelectrics* 7 (Elsevier Science Publishers Ltd.— 1992) pp. 733-739.

Wilke, D. et al., 1992, "Application of Redox Mediators in Enzyme Electrodes," Proc. Conf. Trends Electrochem. Biosens., pp. 155-161.

(56) References Cited

OTHER PUBLICATIONS

Yao, T., 1983, Analytica Chim. Acta, 148:27-33.
European Office Action dated Mar. 25, 2013 for European Patent Application No. 07810763.8.
PCT International Search Report and Written Opinion dated Apr. 28, 2011 (International Appln. No. PCT/US2010/060883).
Japanese Office Action dated Jul. 24, 2012 for JP application No. 2009-521819.

* cited by examiner

R = H, CH₃, CH₂CH₃

R' = H, OH, NH₂, CH₃, C₂H₅, C₃H₇, C₂H₄OH, C₂H₄NH₂

R = H, CH₃, CH₂CH₃

R' = H, OH, NH₂, CH₃, C₂H₅, C₃H₇, C₂H₄OH, C₂H₄NH₂

2-methacryloyloxyethyl phosphorylcholine (MPC)

Vinyl pyrrolidone

R = H, CH$_3$, CH$_2$CH$_3$
R' = CH$_3$, C$_2$H$_5$

Vinyl Acetate

R = H, CH$_3$, CH$_2$CH$_3$

R = CH$_3$, C$_2$H$_5$
dimethyl/ethyl methacrylamide

R = H, CH$_3$, CH$_2$CH$_3$

R' = H, CH$_3$, C$_2$H$_5$, C$_3$H$_7$, C$_2$H$_4$OH, C$_2$H$_4$NH$_2$, SiC$_3$H$_9$

R = H, CH$_3$, C$_2$H$_5$

R' = CH$_3$, C$_2$H$_5$, C$_3$H$_7$, C$_2$H$_4$ (C$_6$H$_5$), C$_2$H$_4$CF$_3$

ANALYTE SENSORS AND METHODS FOR MAKING AND USING THEM

CROSS REFERENCE TI RELATED APPLICATIONS

This application is related to U.S. patent application Ser. No. 10/273,767 filed Oct. 18, 2002 (published as US-2004-0074785-A1), U.S. patent application Ser. No. 10/861,837, filed Jun. 4, 2004, U.S. patent application Ser. No. 11/301,512, filed Dec. 13, 2005, and U.S. patent application Ser. No. 11/397,543, filed Apr. 4, 2006, the contents of each of which are incorporated herein by reference.

BACKGROUND OF THE INVENTION

1. Field of the Invention

This invention relates to analyte sensors such as glucose sensors used in the management of diabetes and materials for making such sensors, for example comb-copolymeric membrane materials.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

Equation 1

Equation 2
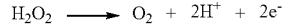

The glucose oxidase is used to catalyze the reaction between glucose and oxygen to yield gluconic acid and hydrogen peroxide (equation 1). The $H_2O_2$ reacts electrochemically as shown in equation 2, and the current is measured by a potentiostat.

A key problem in the use of this type of glucose sensor in the body is that the oxygen concentration in human body is too low compared with glucose concentration. Several approaches to solve this problem have been attempted in the past. The simplest way is to make a porous membrane from a fully oxygen permeable material. However, the small amount of enzyme disposed for glucose tends to become inactivated (see, e.g. U.S. Pat. No. 4,484,987, the contents of which are incorporated by reference). Another approach is to make homogenous polymer membrane with hydrophobic and hydrophilic regions leading to limited control of oxygen and glucose permeability (see, e.g. U.S. Pat. Nos. 5,428,123; 5,322,063, 5,476,094, the contents of which are incorporated by reference).

A key to stable and high sensitivity enzyme biosensors is that the sensor output must be limited only by the analyte of interest, not by any co-substrates or kinetically controlled parameters such as diffusion. In order to maximize the output current of biosensor, oxygen diffusion should be as high as possible while maintaining oxygen excess at the reaction surface. Silicone has the highest permeability to oxygen of any polymeric materials, but it is useless to directly use it as a membrane for glucose sensor because it is completely impermeable to glucose. Van Antwerp et al. have successfully developed linear random polyurea membranes with silicone hydrophobic component offering high oxygen permeability and with hydrophilic component offering limited glucose permeability (see e.g. U.S. Pat. Nos. 5,777,060, 5,882,494 and 6,642,015 B2). However, only polyethylene glycol (PEG) containing hydrophilic materials were considered optimal constituents for such membranes.

SUMMARY OF THE INVENTION

The invention disclosed herein provides sensors such as amperometric glucose sensors and improved materials for use with such sensors. Embodiments of the invention include a sensor having a plurality of layered elements including an analyte limiting membrane comprising a silicone based comb-like copolymer with silicone material as side chain offering high oxygen permeability, and with other hydrophilic material as either side chain or main chain offering controllable glucose permeability. Such polymeric membranes are particularly useful in the construction of electrochemical sensors for in vivo use, and embodiments of the invention include specific biosensor configurations that incorporate these polymeric membranes. The membrane embodiments of the invention allow for a combination of desirable properties including oxygen and glucose permeability. Due to the existence of silicone material, these polymeric membranes possess good mechanical properties for use as an outer polymeric membrane, and glucose sensors that incorporate such polymeric membranes show good in-vivo performance. The current invention allows artisans to employ of a wide variety of different hydrophilic materials in addition to traditionally utilized materials such as polyethylene glycol (PEG).

The invention disclosed herein has a number of embodiments. One embodiment is an analyte sensor apparatus for implantation within a mammal, the analyte sensor apparatus comprising a base layer, a conductive layer disposed upon the base layer wherein the conductive layer includes a working electrode, an analyte sensing layer disposed on the conductive layer, wherein the analyte sensing layer detectably alters the electrical current at the working electrode in the conductive layer in the presence of an analyte; and an analyte modulating layer disposed on the analyte sensing layer, wherein the analyte modulating layer modulates the diffusion of the analyte therethrough; the analyte modulating layer comprising a hydrophilic comb-copolymer having a central chain and a plurality of side chains coupled to the central chain, wherein at least one side chain comprises a silicone moiety. Typically, the at least one side chain moiety comprises a Silicon atom covalently bound to an Oxygen atom (—Si—O—). Optionally, at least one side chain is hydrophilic. Optionally, at least one side chain is hydrophobic. Certain embodiments of the invention include both hydrophilic and hydrophobic residues. In some embodiments of the invention, the central chain to which the side chains are coupled is hydrophilic.

Another embodiment of the invention is a method of making a sensor apparatus for implantation within a mammal comprising the steps of: providing a base layer; forming a conductive layer on the base layer, wherein the conductive layer includes a working electrode; forming an analyte sensing layer on the conductive layer, wherein the analyte sensing layer includes a composition that can alter the electrical current at the working electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough, the analyte modulating layer comprising a hydrophilic comb-copolymer having a central chain and a plurality of side chains coupled to the central chain, wherein at least one side chain comprises a silicone moiety; and forming a cover layer disposed on at least a portion of the analyte modulating layer, wherein the cover layer further includes an aperture over at least a portion of the analyte modulating layer.

Yet another embodiment of the invention is a method of sensing an analyte within the body of a mammal, the method comprising implanting an analyte sensor in to the mammal, the analyte sensor comprising: a base layer; a conductive layer disposed upon the base layer wherein the conductive layer includes a working electrode; an analyte sensing layer disposed on the conductive layer, wherein the analyte sensing layer detectably alters the electrical current at the working electrode in the conductive layer in the presence of an analyte; an analyte modulating layer disposed on the analyte sensing layer, wherein the analyte modulating layer modulates the diffusion of the analyte therethrough; the analyte modulating layer comprising a hydrophilic comb-copolymer having a central chain and a plurality of side chains coupled to the central chain, wherein at least one side chain comprises a silicone moiety; and sensing an alteration in current at the working electrode and correlating the alteration in current with the presence of the analyte, so that the analyte is sensed.

The invention also provides additional articles of manufacture including sensor elements, sensor sets and kits. In one such embodiment of the invention, a kit and/or sensor element or set, useful for the sensing an analyte as is described above, is provided. The kit and/or sensor set typically comprises a container, a label and a sensor as described above. The typical embodiment is a kit comprising a container and, within the container, an analyte sensor apparatus having a design as disclosed herein and instructions for using the analyte sensor apparatus.

Additional embodiments of the invention include the comb-copolymer itself, for example a composition of matter comprising a hydrophilic comb-copolymer having a central chain and a plurality of side chains coupled to the central chain, wherein at least one side chain comprises a silicone moiety. Typically, the at least one side chain moiety comprising a silicone moiety comprises a Silicon atom covalently bound to an Oxygen atom (—Si—O—). In certain embodiments of the invention, the backbone or main chain of at least one side chain comprises 2, 3, 4, 5, 6, 7, 8, 9, 10, 11, 12, 13, 14 or 15 atoms. Optionally, at least one side chain is hydrophilic. Optionally, at least one side chain is hydrophobic. Certain embodiments of the invention include both hydrophilic and hydrophobic residues. In some embodiments of the invention, the central chain to which the side chains are coupled is hydrophilic. In one illustrative embodiment of the invention, the central chain comprises a polyvinyl polymer, such as a polyvinyl acetate, acrylate, acrylamide, acrylonitrile or pyrrolidone subunits. In another illustrative embodiment of the invention, the central chain comprises polyethylene or polypropylene subunits. Typically, these compositions are made by a process comprising free radical copolymerization.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE EMBODIMENTS

Figure 1:
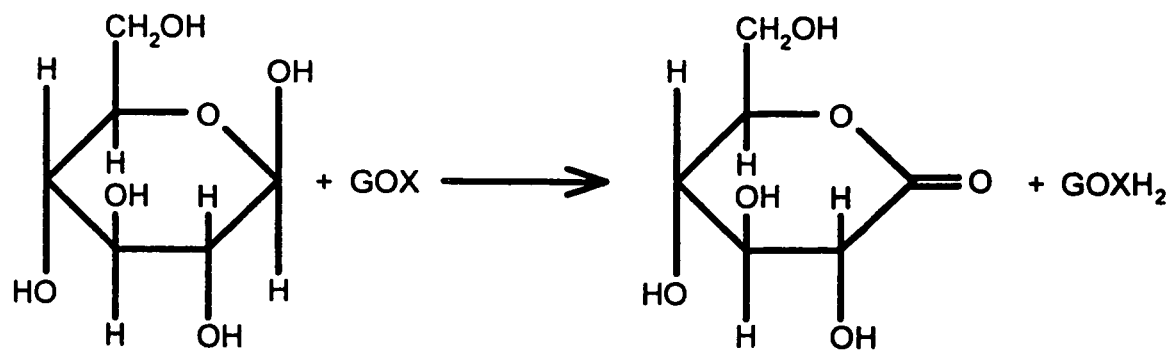
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H+ + O_2 + 2e^-$).
Figure 1:
Figure 1:
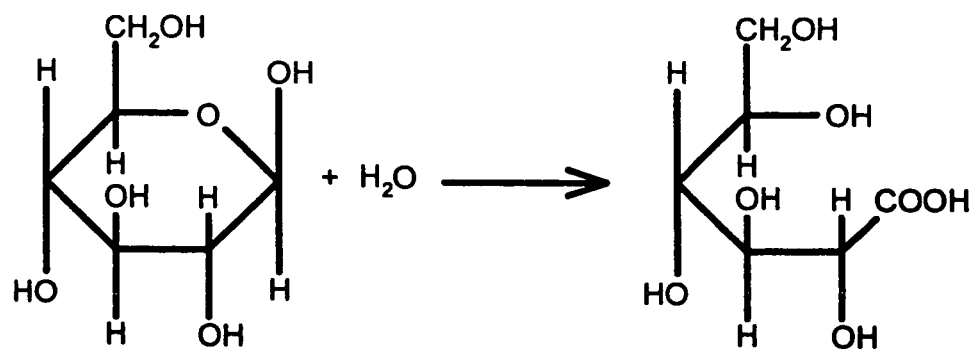

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed.

Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The terms "electrochemically reactive surface" and "electroactive surface" as used herein are broad terms and are used in their ordinary sense, including, without limitation, the surface of an electrode where an electrochemical reaction takes place. In one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. In an illustrative embodiment, the sensing region can comprise a non-conductive body, a working electrode, a reference electrode, and a counter electrode passing through and secured within the body forming electrochemically reactive surfaces on the body and an electronic connective means at another location on the body, and a one or more layers covering the electrochemically reactive surface.

The terms "electrical potential" and "potential" as used herein, are broad terms and are used in their ordinary sense, including, without limitation, the electrical potential difference between two points in a circuit which is the cause of the flow of a current. The term "system noise," as used herein, is a broad term and is used in its ordinary sense, including, without limitation, unwanted electronic or diffusion-related noise which can include Gaussian, motion-related, flicker, kinetic, or other white noise, for example.

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. Optionally, the membrane is an analyte modulating layer comprising a hydrophilic comb-copolymer having a central chain and a plurality of side chains coupled to the central chain, wherein at least one side chain comprises a silicone moiety. The product is then measured using electrochemical methods and thus the output of an electrode system functions as a measure of the analyte. In some embodiments, the sensor can use an amperometric, coulometric, conductimetric, and/or potentiometric technique for measuring the analyte.

Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 and WO 03/074107, and European Patent Application EP 1153571, the contents of each of which are incorporated herein by reference.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their biospecificity. For example, a first class of glucose sensor designs use a very thin (<1 micron) layer of glucose oxidase (GOx) and bovine serum albumin that is either spray or spin coated onto the working electrode and cross-linked with glutaraldehyde. Alternatively, a second class of glucose sensor design employs a thick (~1 mm) hydrogel known as the Sensor Matrix Protein (SMP), which typically consists of an enzyme such as GOx and human serum albumin cross-linked together with a cross-linking agent such as glutaraldehyde. Relative to each other, the immobilized enzyme configurations of the two above-noted classes of sensor designs possess different advantages that serve to increase operational sensor life. Due to the close proximity of the immobilized GOx to the peroxide-consuming electrode, the first class of sensor designs are believed to possess significantly decreased enzyme deactivation rate constants. In comparison, the thick SMPs utilized in the second class of sensor designs can incorporate orders of magnitude more enzyme than the first class.

Many sensor designs utilize a matrix (or a plurality of matrices) such as an enzymatic hydrogel matrix to function. The term "matrix" is used herein according to its art-accepted meaning of something within or from which something else originates, develops, takes form and/or is found. An exemplary enzymatic hydrogel matrix for example typically comprises a bio-sensing enzyme (e.g. glucose oxidase or lactate oxidase) and human serum albumin proteins that have been cross-linked together with a crosslinling agent such as glutaraldehyde to form a polymer network. This network is then swollen with an aqueous solution to form an enzymatic hydrogel matrix. The degree of swelling of this hydrogel frequently increases over a time-period of several weeks, and is presumably due to the degradation of network cross-links. Regardless of its cause, an observed consequence of this swelling is the protrusion of the hydrogel outside of the hole or "window" cut into the outer sensor tubing. This causes the sensor dimensions to exceed design specifications and has a negative impact on its analytical performance.

Embodiments of the invention disclosed herein provide sensor elements having enhanced material properties and sensors constructed from such elements. The disclosure further provides methods for making and using such sensors. While some embodiments of the invention pertain to glucose and/or lactate sensors, a variety of the elements disclosed herein (e.g. electrodes and electrode designs) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

In typical embodiments of the present invention, the transduction of the analyte concentration into a processable signal is by electrochemical means. These transducers may include any of a wide variety of amperometric, potentiometric, or conductimetric base sensors known in the art. Moreover, the microfabrication sensor techniques and materials of the instant invention may be applied to other types of transducers (e.g., acoustic wave sensing devices, thermistors, gas-sensing electrodes, field-effect transistors, optical and evanescent field wave guides, and the like) fabricated in a substantially nonplanar, or alternatively, a substantially planar manner. A useful discussion and tabulation of transducers which may be exploited in a biosensor as well as the kinds of analytical applications in which each type of transducer or biosensor, in general, may be utilized, is found in an article by Christopher R. Lowe in Trends in Biotech. 1984, 2(3), 59-65.

Specific aspects of the invention are discussed in detail in the following sections.

I. Typical Elements, Configurations and Analyte Sensors of the Invention

A. Optimized Sensor Elements of the Invention

Embodiments of the sensors disclosed herein incorporate one or more sensor elements having enhanced material properties. Embodiments of the invention include sensors comprising these elements and well methods for making and using them. Embodiments of the invention disclosed herein include comb copolymeric membranes designed to optimize factors including the reactivity, sensitivity, functioning and lifespan of the analyte sensors. Certain specific embodiments of the invention are designed to optimize the chemical reactions that function in the sensing of an analyte of interest (e.g. by optimizing the stoichiometry of the reactants). The optimized embodiments of the invention disclosed herein can be utilized and/or applied to a wide variety of sensor methods and designs. The following sections describe illustrative sensor elements, sensor configurations and methodological embodiments of the invention.

Embodiments of the invention are designed to enhance the ability of a sensor to perform reactions associated with sensing the analyte (e.g. by controlling the stoichiometry of the reactants). As discussed in detail below, embodiments of the invention include analyte sensors having a plurality of adjoining layers consisting of different functional constituents. In this context, the invention disclosed herein provides sensors such as amperomettic glucose sensors and improved materials for use with such sensors. Embodiments of the invention include a sensor having a plurality of layered elements including an analyte limiting membrane comprising a silicone based comb-like copolymer with silicone material as side chain offering high oxygen permeability, and with other hydrophilic material as either side chain or central chain offering controllable glucose permeability. Such polymeric membranes are particularly useful in the construction of electrochemical sensors for in vivo use and embodiments of the invention include specific biosensor configurations that incorporate these polymeric membranes. The membrane embodiments of the invention allow for a combination of desirable properties including high oxygen and glucose permeability.

One embodiment of the present invention provides a silicone-based comb-copolymer for use in covering an analyte sensor, e.g. a glucose biosensor, particularly one intended for in vivo use. In the membranes disclosed herein, the silicone component has very low glass transition temperature (e.g. below room temperature and typically below 0° C.) and very high oxygen permeability (e.g. $1 \times 10^{-7}$ cm$^2$/sec), characteristics selected to provide advantages such as good mechanical property, higher signal-to-noise ratio, high stability, and highly accurate analysis in in-vivo environments.

Typical embodiments of the invention include a composition of matter comprising a hydrophilic comb-copolymer having a central chain and a plurality of side chains coupled to the central chain, wherein at least one side chain comprises a silicone moiety. As is known in the art, a comb-copolymer is one having a structure analogous to a hair comb which has a central backbone to which a plurality of teeth are attached. Such comb-copolymers have a central or main chain (that is roughly analogous to the backbone of the comb) and a plurality of side chains (that are roughly analogous to the teeth of a comb) that branch off of this central chain. This comb-copolymeric structure is shown for example at the bottom of FIG. 3, where the horizontal (—C—CH$_2$—C—CH$_2$—C—CH$_2$—)$_p$ portion of the molecule is the central or main chain and the vertical for example (—C—O—C—) portions of the molecule comprise the side chains. These side chains can further have main chain to which various atoms and moieties are attached, for example the vertical (—C—O—C—C—C—Si—O—) side chain shown on the right side of the molecule shown at the bottom of FIG. 3. For example the horizontal central chain of the side chain shown in this figure has hydrogen and/or methyl atoms and moieties attached thereto. In certain embodiments of the invention, the backbone of at least 1, 2, 3, 4, or 5 different side chains comprises 2, 3, 4, 5, 6, 7, 8, 9, 10, 11, 12, 13, 14 or 15 atoms.

The comb-copolymers that can be used as membranes in the sensors disclosed herein have a number of embodiments. Typically in such embodiments, at least one side chain moiety comprising a silicone moiety comprises a Silicon atom covalently bound to an Oxygen atom (—Si—O—). In some embodiments of the invention, at least one side chain that branches off of the central chain is hydrophilic. In some embodiments of the invention, at least one side chain that branches off of the central chain is hydrophobic. In some embodiments of the invention, at least one side chain that branches off of the central chain is hydrophilic and at least one side chain that branches off of the central chain is hydrophobic. Optionally, the central chain is hydrophilic. Alternatively, the central chain can be hydrophobic, with hydrophilic properties being provided by the side chains.

In certain embodiments of the invention, the central chain comprises a polyvinyl polymer, i.e. a composition formed by polymerizing various vinyl (e.g. CH2=CH—) monomers. Examples include polyvinyl chlorides, polyvinyl acetates, and polyvinyl alcohols. Typically, such polyvinyl polymers comprise polyvinyl acetate, acrylate, acrylamide, acrylonitrile or pyrrolidone subunits. Alternatively the central chain can comprise polyethylene or polypropylene subunits. As is known in the art, such comb copolymers can be made from a variety of different methods, for example a process comprising free radical copolymerization. Typically, the comb-copolymer is made from free radical polymerization of at least one silicone material, and at least one hydrophilic material. Optionally, one or more hydrophobic materials are also used for specific applications and contexts. Illustrative methods and materials for use in making the polymeric compositions of the invention are described for example in U.S. Pat. Nos. 6,887,962, 6,809,141, 6,093,781, 5,807,937 5,708,115, 5,091,480, 5,079,298, 5,061,772, 5,503,461, 6,538,091 and 6,527,850 7,029,688, 7,029,688, 7,001,949; and U.S. Patent Application Nos. 20050143546, 20040024144 and 20030181619, 20040024144 the contents of each are herein incorporated by reference. Polymers can be coated onto biosensors using a variety of methods known in the art, for example those described in U.S. Pat. Nos. 5,882,494, 6,965, 791, 6,934,572, 6,814,845, 6,741,877, 6,594,514, 6,477,395, 6,927,246, 5,422,246, 5,286,364, 6,927,033, 5,804,048, 7,003,340, 6,965,791; and U.S. Patent Application Nos. 20060128032, 20060068424, 20050208309, 20040084307, 20030171506, 20030069383, and 20010008931, the contents of each are herein incorporated by reference.

Embodiments of the invention include sensors having a membrane comprising the polymeric compositions described herein. An illustrative embodiment is an analyte sensor apparatus for implantation within a mammal, the analyte sensor apparatus comprising a base layer, a conductive layer disposed upon the base layer wherein the conductive layer includes a working electrode, an analyte sensing layer disposed on the conductive layer, wherein the analyte sensing layer detectably alters the electrical current at the working electrode in the conductive layer in the presence of an analyte, an analyte modulating layer disposed on the analyte sensing layer, wherein the analyte modulating layer modulates the diffusion of the analyte therethrough; the analyte modulating layer comprising a hydrophilic comb-copolymer having a central chain and a plurality of side chains coupled to the central chain, wherein at least one side chain comprises a silicone moiety. Typically, the at least one side chain moiety comprises a Silicon atom covalently bound to an Oxygen atom (—Si—O—). Optionally, at least one side chain is hydrophilic, at least one side chain is hydrophobic or at least one chain is hydrophilic, and in addition, at least one chain is hydrophobic. Optionally, the central chain is hydrophilic. Alternatively, the central chain can be hydrophobic, with hydrophilic properties being provided by the side chains. In such analyte sensor apparatus, the membrane having this structure confers a number of desirable properties. Typically for example, the analyte modulating layer has a glucose diffusion coefficient ($D_{glucose}$) of from $1\times10^{-9}$ cm$^2$/sec to $1\times10^{-7}$ cm$^2$/sec. In addition, typically, the analyte modulating layer has a oxygen diffusion coefficient ($D_{oxygen}$) to glucose diffusion coefficient ($D_{glucose}$) ratio ($D_{oxygen}/D_{glucose}$) of 5 to 2000.

Optionally the analyte sensor apparatus further includes additional layers such as a protein layer disposed between the analyte sensing layer and the analyte modulating layer, and/or a cover layer disposed on at least a portion of the analyte modulating layer, wherein the cover layer further includes an aperture that exposes at least a portion of the analyte modulating layer to a solution comprising the analyte to be sensed. In certain embodiments of the invention, the analyte sensing layer comprises an enzyme selected from the group consisting of glucose oxidase, glucose dehydrogenase, lactate oxidase, hexoltinase and lactose dehydrogenase.

Another embodiment of the invention is a method of making a sensor apparatus for implantation within a mammal comprising the steps of providing a base layer; forming a conductive layer on the base layer, where in the conductive layer includes a working electrode; forming an analyte sensing layer on the conductive layer, wherein the analyte sensing layer includes a composition that can alter the electrical current at the working electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough, the analyte modulating layer comprising a hydrophilic comb-copolymer having a central chain and a plurality of side chains coupled to the central chain (typically comprising 2, 3, 4, 5, 6, 7, 8, 9, 10, 11, 12, 13, 14 or 15 atoms), wherein at least one side chain comprises a silicone moiety; and then forming a cover layer disposed on at least a portion of the analyte modulating layer, wherein the cover layer further includes an aperture over at least a portion of the analyte modulating layer. In this method, typically, the analyte modulating layer has a glucose diffusion coefficient ($D_{glucose}$) of from $1\times10^{-9}$ cm$^2$/sec to $200\times10^{-9}$ cm$^2$/sec, and a oxygen diffusion coefficient ($D_{oxygen}$) to glucose diffusion coefficient ($D_{glucose}$) ratio ($D_{oxygen}/D_{glucose}$) of from 5 to 2000.

Another embodiment of the invention is a method of sensing an analyte within the body of a mammal, the method comprising implanting an analyte sensor in to the mammal, the analyte sensor comprising a base layer; a conductive layer disposed upon the base layer wherein the conductive layer includes a working electrode; an analyte sensing layer disposed on the conductive layer, wherein the analyte sensing layer detectably alters the electrical current at the working electrode in the conductive layer in the presence of an analyte; an analyte modulating layer disposed on the analyte sensing layer wherein the analyte modulating layer modulates the diffusion of the analyte therethrough; the analyte modulating layer comprising a hydrophilic comb-copolymer having a central chain and a plurality of side chains coupled to the central chain, wherein at least one side chain comprises a silicone moiety; and sensing an alteration in current at the working electrode and correlating the alteration in current with the presence of the analyte, so that the analyte is sensed.

Another embodiment of the invention is a kit comprising a container and, within the container, an analyte sensor apparatus comprising a base layer; a conductive layer disposed upon the base layer; wherein the conductive layer includes a working electrode an analyte sensing layer disposed on the conductive layer; wherein the analyte sensing layer detectably alters the electrical current at the working electrode in the conductive layer in the presence of an analyte; an analyte modulating layer disposed on the analyte sensing layer, wherein the analyte modulating layer modulates the diffusion of the analyte therethrough; the analyte modulating layer comprising a hydrophilic comb-copolymer having a central chain and a plurality of side chains coupled to the central chain, wherein at least one side chain comprises a silicone moiety; and instructions for using the analyte sensor apparatus.

Figure 3:
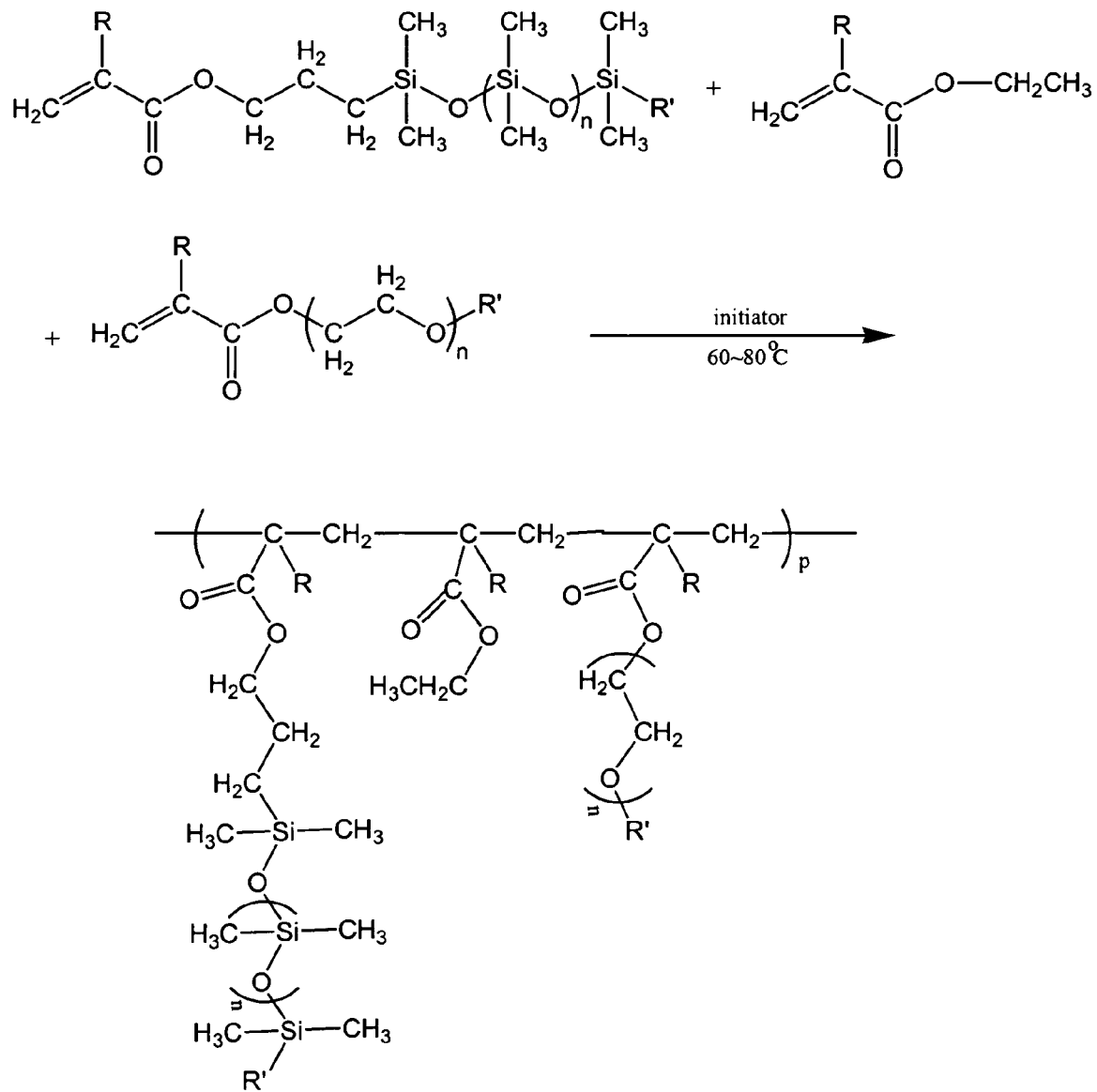
FIG. 3 shows the exemplary polymerization reaction from a silicone material, a hydrophilic moiety and a hydrophobic moiety.
Figure 4:
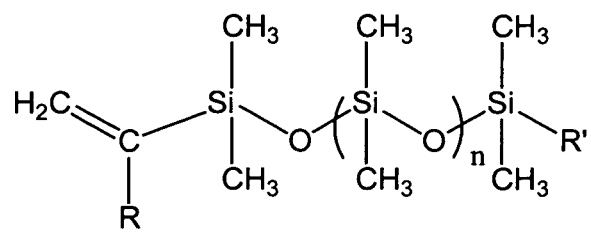
FIG. 4 shows exemplary silicone materials in the present invention.
Figure 4:
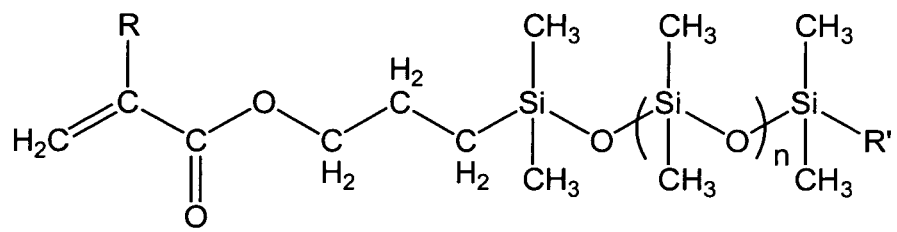
Figure 5:
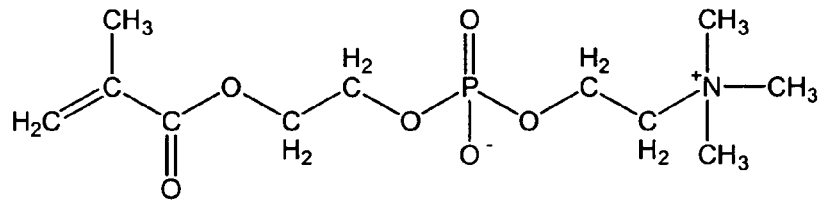
FIG. 5 shows exemplary hydrophilic materials in the present invention.
Figure 5:
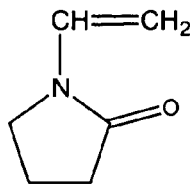
Figure 5:
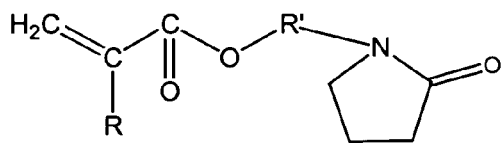
Figure 5:
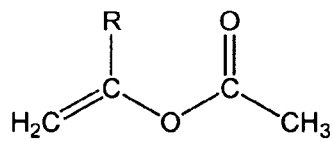
Figure 5:
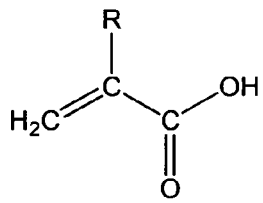
Figure 5:
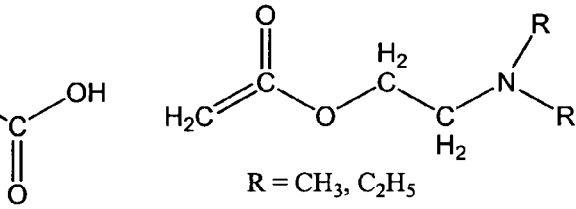
Figure 5:
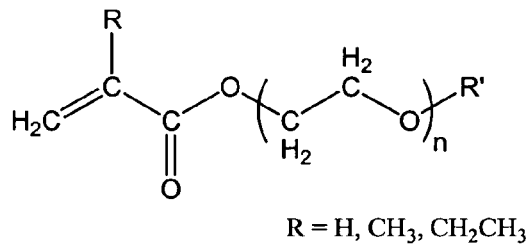
Figure 5:
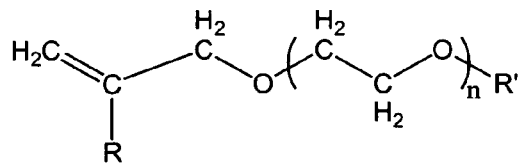
Figure 6:
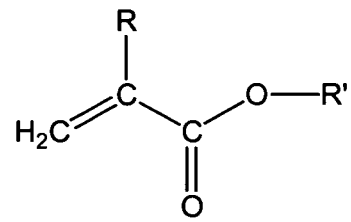
FIG. 6 shows exemplary hydrophobic materials in the present invention.

As illustrated in the Examples below, the membranes of present invention can be prepared by free radical co-polymerization of silicone material and other hydrophilic/hydrophobic moieties (FIG. 3). Typical silicone materials which are used in the invention are those which have multi —Si—O— repeat units and vinyl or acryl reactive functional end groups, which may also contain some other functional groups such as —OH, —NH$_2$, —COOH. The typical silicone materials used in this invention are mono vinyl terminated polydimethylsiloxane and mono methacryloxypropyl terminated polydimethylsiloxane (see FIG. 4). The typical hydrophilic moieties include all water-soluble materials containing vinyl or acryl reactive functional groups. FIG. 5 shows some illustrative hydrophilic moieties used in this invention such as 2-methacryloyloxyethyl phosphorylcholine, n-vinyl pyrrolidone, dihydroxypropyl methacrylate, dimethyl methacrylamide, 2-hydroxyethyl methacrylate, poly(ethylene glycol)methyl ether methacrylate, and mono ally mono trimethylsiloxy terminated polyethylene oxide. Typical hydrophobic materials used in this invention could be any non water-soluble moieties with vinyl or aryl reactive functional groups (FIG. 6). Preferable embodiments utilize methyl methacrylate, 2-phenylethyl acrylate and 4-phenylbutyl methacrylate.

B. Diagrammatic Illustration of Typical Sensor Configurations

Figure 2:
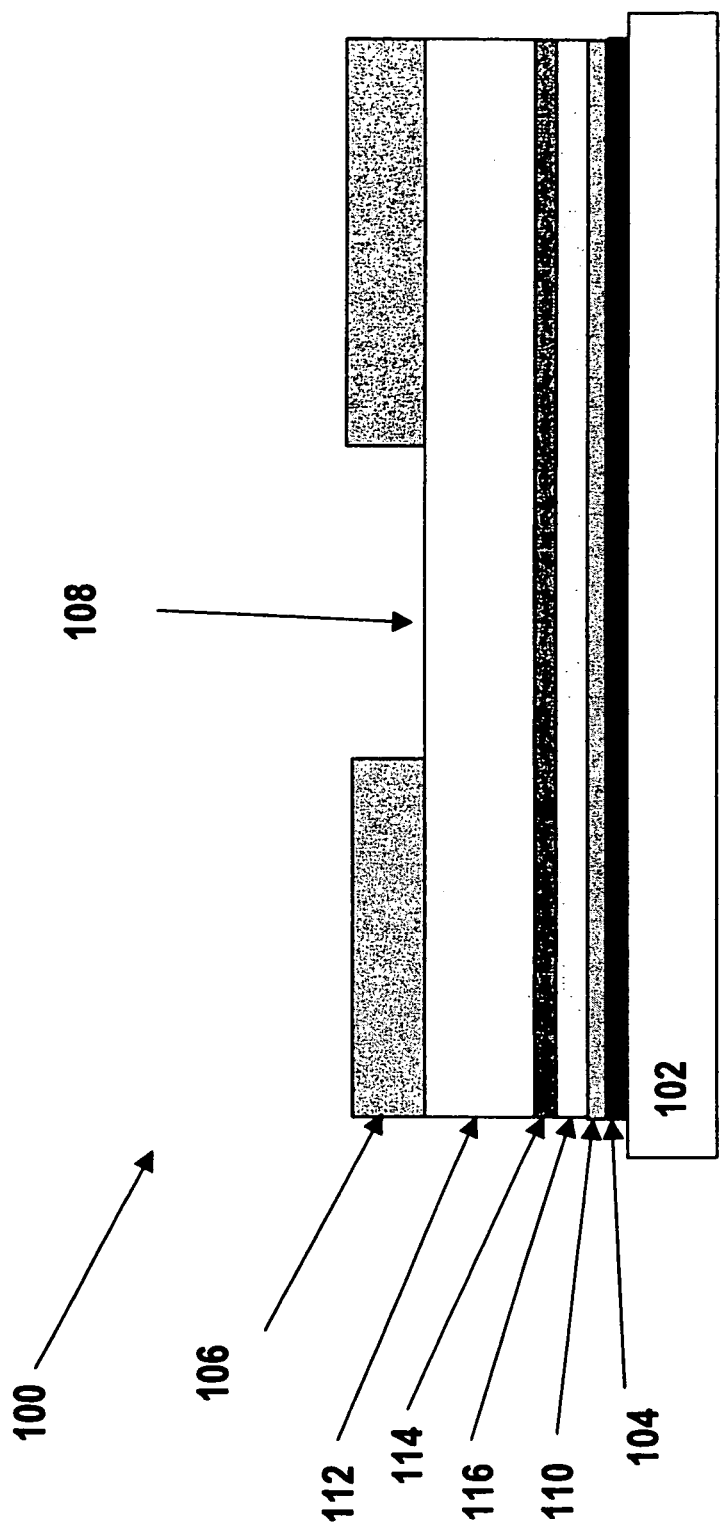
FIG. 2 provides a diagrammatic view of a typical analyte sensor configuration of the current invention.

FIG. 2 illustrates a cross-section of a typical sensor structure 100 of the present invention. The sensor is formed from a plurality of components that are typically in the form of layers of various conductive and non-conductive constituents disposed on each other according to a method of the invention to produce a sensor structure. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. In certain embodiments, the base layer 102 and/or the conductive layer 104 can be constructed to produce electrodes having a configuration where the electrochemically reactive surface area of an electrode is disposed on the geometric feature so that the electrochemically reactive surface area is greater than if it was disposed on a flat surface.

Typically the conductive layer 104 comprises one or more electrodes. An operating sensor 100 typically includes a plurality of electrodes such as a working electrode, a counter electrode and a reference electrode. Other embodiments may also include an electrode that performs multiple functions, for example one that functions as both as a reference and a counter electrode. Still other embodiments may utilize a separate reference element not formed on the sensor. Typically these electrodes are electrically isolated from each other, while situated in close proximity to one another.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating is optionally disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. Typically, the sensor chemistry layer 110 is an enzyme layer. Most typically, the sensor chemistry layer 110 comprises an enzyme capable of producing and/or utilizing oxygen and/or hydrogen peroxide, for example the enzyme glucose oxidase. Optionally the enzyme in the sensor chemistry layer is combined with a second carrier protein such as human serum albumin, bovine serum albumin or the like. In an illustrative embodiment, an enzyme such as glucose oxidase in the sensor chemistry layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

The analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include spin coating processes, dip and dry processes, low shear spraying processes, ink-jet printing processes, silk screen processes and the like. Most typically the thin analyte sensing layer 110 is applied using a spin coating process.

Typically, the analyte sensing layer 110 is coated with one or more additional layers. Optionally, the one or more additional layers includes a protein layer 116 disposed upon the analyte sensing layer 110. Typically, the protein layer 116 comprises a protein such as albumin or the like. Typically, the protein layer 116 comprises human serum albumin. In some embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art. Typically, the analyte modulating layer comprises a hydrophilic comb-copolymer having a central chain and a plurality of side chains coupled to the central chain, wherein at least one side chain comprises a silicone moiety.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

C. Typical Analyte Sensor Constituents

The following disclosure provides examples of typical elements/constituents used in the sensors of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor).

Base Constituent

Sensors of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as water impermeability and hermeticity. Some materials include metallic ceramic and polymeric substrates or the like. In certain embodiments, the base constituent and/or the conductive constituent can be constructed to produce electrodes having a configuration where the electrochemically reactive surface area of an electrode is disposed on the geometric feature so that the electrochemically reactive surface area is greater than if it was disposed on a flat surface.

The base constituent may be self-supporting or further supported by another material as is known in the art. In one embodiment of the sensor configuration shown in FIG. 2, the base constituent 102 comprises a ceramic. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 25 microns). Alternatively, one can utilize a nonconductive ceramic, such as alumina, in thin constituents, e.g., less than about 25 microns.

Embodiments of invention disclosed herein provide individual elements and sensors which exhibit a combination of the independent advantages found in each of the two sensor classes disclosed above. For example a first embodiment of the invention immobilizes an enzyme onto a thick (1-1,000 micron), porous substrate which functions as an electrode in the sensor. In this context, the porous electrode is designed to exhibit an increased surface area, for example by constructing it from a lattice of equal-sized adjoining spheres. In one illustrative embodiment, glucose oxidase is immobilized on a thick (1-1,000 micron), porous metallic substrate that is manufactured from a lattice of equal-sized adjoining spheres and which function as a hydrogen peroxide-consuming electrode.

In another embodiment of the invention disclosed herein the hydrogel typically utilized in a variety of analyte sensors is replaced with an essentially rigid, non-swelling porous enzyme-polymer matrix. In this embodiment, bio-sensing enzymes can be stably immobilized via covalent bonding to a rigid, macroporous polymer that has optionally been molded into a specified shape. In this context, molded continuous rods of macroporous polymers have been developed for use as chromatographic separation media (see, e.g. U.S. Pat. No. 5,453,185 and WO 93/07945). Suitable polymers are essentially incompressible and do not change their overall size in response to changes in their solvating environment. Moreover, adjustments to the polymerization conditions can be used to control the morphology of the pores. Hence, highly porous (50-70%) polymers can be created that possess significant volume fractions of pores in the ranges of 1-100 nm and 100-3,000 nm (i.e. 20% and 80%, respectively). Polymers with this type of pore structure possess a very high specific surface area (i.e. 185 $m^2/g$), and are expected to allow for high enzyme immobilization densities (1-100 mg/mL).

Various methods and compositions for making and using the above-noted porous matrices as well as analyte sensors which incorporate such matrices are further described herein.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically, for in vivouse the analyte sensors of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperomettic detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Examples of interference rejection constituents include one or more layers or coatings of compounds such as hydrophilic polyurethanes, cellulose acetate (including cellulose acetate incorporating agents such as poly(ethylene glycol), polyethersulfones, polytetrafluoroethylenes, the perfluoronated ionomer Nafion™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference.

Analyte Sensing Constituent

The electrochemical sensors of the invention include an analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent. As discussed for example in U.S. patent application Ser. No. 10/273,767 (incorporated herein by reference) extremely thin sensor chemistry constituents are typical and can be applied to the surface of the electrode matrix by processes known in the art such as spin coating. In an illustrative embodiment, a glucose oxidase/alburdin is prepared in a physiological solution (e.g., phosphate buffered saline at neutral pH) with the albumin being present in a range of about 0.5%-10% by weight. Optionally the stabilized glucose oxidase constituent that is formed on the analyte sensing constituent is very thin as compared to those previously described in the art, for example less than 2, 1, 0.5, 0.25 or 0.1 microns in thickness. One illustrative embodiment of the invention utilizes a stabilized glucose oxidase constituent for coating the surface of an electrode wherein the glucose oxidase is mixed with a carrier protein in a fixed ratio within the constituent, and the glucose oxidase and the carrier protein are distributed in a substantially uniform manner throughout the constituent. Typically the constituent is less than 2 microns in thickness. For purposes of clarity, it should be noted that this may not apply to certain embodiments of the invention where the analyte sensing constituent is disposed on a porous electrode. For example, in a porous electrode that is 100 microns thick, with 3 micron size pores that are filled with GOx, an enzyme layer can be greater 2 microns.

Surprisingly, sensors having these extremely thin analyte sensing constituents have material properties that exceed those of sensors having thicker coatings including enhanced longevity, linearity, regularity as well as improved signal to noise ratios. While not being bound by a specific scientific theory, it is believed that sensors having extremely thin analyte sensing constituents have surprisingly enhanced characteristics as compared to those of thicker constituents because in thicker enzyme constituents only a fraction of the reactive enzyme within the constituent is able to access the analyte to be sensed. In sensors utilizing glucose oxidase, the thick coatings produced by electrodeposition may hinder the ability of hydrogen peroxide generated at the reactive interface of a thick enzyme constituent to contact the sensor surface and thereby generate a signal.

As noted above, the enzyme and the second protein are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde, including, but not limited to, an amine reactive, homofunctional, cross-linking reagent such as Disuccinilmidyl Suberate (DSS). Another example is 1-Ethyl-3(3-Dimethylaminopropyl) Carbodiimide (EDC), which is a zero-length cross-linker. EDC forms an amide bond between carboxylic acid and amine groups. Other suitable cross-linkers also may be used, as will be evident to those skilled in the art.

The GOx and/or carrier protein concentration may vary for different embodiments of the invention. For example, the GOx concentration may be within the range of approximately 50 mg/ml (approximately 10,000 U/ml) to approximately 700 mg/ml (approximately 150,000 U/ml). Typically the GOx concentration is about 115 mg/ml (approximately 22,000 U/ml). In such embodiments, the HSA concentration may vary between about 0.5%-30% (w/v), depending on the GOx concentration. Typically the HSA concentration is about 1-10% w/v, and most typically is about 5% w/v. In alternative embodiments of the invention, collagen or BSA or other structural proteins used in these contexts can be used instead of or in addition to HSA. Although GOx is discussed as an illustrative enzyme in the analyte sensing constituent, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, could be used instead of or in addition to HSA.

For embodiments employing enzymes other than GOx, concentrations other than those discussed herein may be utilized. For example, depending on the enzyme employed, concentrations ranging from approximately 10% weight per weight to 70% weight per weight may be suitable. The concentration may be varied not only depending on the particular enzyme being employed, but also depending on the desired properties of the resulting protein matrix. For example, a certain concentration may be utilized if the protein matrix is to be used in a diagnostic capacity while a different concentration may be utilized if certain structural properties are desired. Those skilled in the art will understand that the concentration utilized may be varied through experimentation to determine which concentration (and of which enzyme or protein) may yield the desired result.

As noted above, in some embodiments of the invention, the analyte sensing constituent includes a composition (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; (Jan. 7, 1991) the entire contents of which are incorporated herein by reference.

Other useful analyte sensing constituents can be formed to include antibodies whose interaction with a target analyte is capable of producing a detectable signal that can be sensed by the electrically conductive elements after interacting with the target analyte whose presence is to be detected. For example U.S. Pat. No. 5,427,912 (which is incorporated herein by reference) describes an antibody-based apparatus for electrochemically determining the concentration of an analyte in a sample. In this device, a mixture is formed which includes the sample to be tested, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme then hydrolyzes the labeled substrate, resulting in the generation of an electroactive label, which can then be oxidized at the surface of an electrode. A current resulting from the oxidation of the electroactive compound can be measured and correlated to the concentration of the analyte in the sample. U.S. Pat. No. 5,149,630 (which is incorporated herein by reference) describes an electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component. The electron transfer is aided by electron-transfer mediators which can accept electrons from the enzyme and donate them to the electrode or vice versa (e.g. ferrocene) or by electron-transfer promoters which retain the enzyme in close proximity with the electrode without themselves taking up a formal charge. U.S. Pat. No. 5,147,781 (which is incorporated herein by reference) describes an assay for the determination of the enzyme lactate dehydrogenase-5 (LDH5) and to a biosensor for such quantitative determination. The assay is based on the interaction of this enzyme with the substrate lactic acid and nicotine-amine adenine dinucleotide (NAD) to yield pyruvic acid and the reduction product of NAD. Anti-LDH5 antibody is bound to a suitable glassy carbon electrode; this is contacted with the substrate containing LDH5, rinsed, inserted into a NAD solution, connected to an amperometric system, and current changes are measured in the presence of differing concentrations of lactic acid, which are indicative of the quantity of LDH-5. U.S. Pat. No. 6,410,251 (which is incorporated herein by reference) describes an apparatus and method for detecting or assaying one constituting member in a specific binding pair; for example, the antigen in an antigen/antibody pair, by utilizing specific binding such as binding between an antigen and an antibody, together with redox reaction for detecting a label, wherein an oxygen micro-electrode with a sensing surface area is used. In addition, U.S. Pat. No. 4,402,819 (which is incorporated herein by reference) describes an antibody-selective potentiometric electrode for the quantitative determination of antibodies (as the analyte) in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis. For related disclosures, see also U.S. Pat. Nos. 6,703,210, 5,981,203, 5,705,399 and 4,894,253, the contents of which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Constituent

The electrochemical sensors of the invention optionally include a protein constituent disposed between the analyte sensing constituent and the analyte modulating constituent (see, e.g. element 116 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase ($GO_X$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent includes an agent selected for its ability to crosslink a siloxane moiety present in a proximal constituent such as the analyte modulating constituent. In closely related embodiments of the invention, the adhesion promoting constituent includes an agent selected for its ability to crosslink an amine or carboxyl moiety of a protein present in a proximal constituent such a the analyte sensing constituent and/or the protein constituent.

Analyte Modulating Constituent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

As described in detail herein, in certain embodiments of the invention, the analyte modulating constituent comprises a hydrophilic comb-copolymer having a central chain and a plurality of side chains coupled to the central chain, wherein at least one side chain comprises a silicone moiety.

Cover Constituent

The electrochemical sensors of the invention include one or more cover constituents which are typically electrically insulating protective constituents (see, e.g. element 106 in FIG. 2). Typically, such cover constituents are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imagable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Various illustrative embodiments of the invention and their characteristics are discussed in detail in the following sections.

D. Illustrative Embodiments of Analyte Sensor Apparatus and Associated Characteristics The analyte sensor apparatus disclosed herein has a number of embodiments. A general embodiment of the invention is an analyte sensor apparatus for implantation within a mammal. We the analyte sensors are typically designed to be implantable within the body of a mammal, the sensors are not limited to any particular environment and can instead be used in a wide variety of contexts, for example for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include, for example, those used to monitor one or more analytes present in one or more physiological environments in a hospitalized patient.

Sensors of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example, in such implanted oxygen sensor apparatus designs, oxygen noise at the reference sensor can compromise the signal to noise ratio which consequently perturbs their ability to obtain stable glucose readings in this environment. The peroxide sensors of the invention therefore overcome the difficulties observed with such oxygen sensors in non-vascular regions.

Certain peroxide sensor embodiments of the invention further include advantageous long term or "permanent" sensors which are suitable for implantation in a mammal for a time period of greater than 30 days. In particular, as is known in the art (see, e.g. ISO 10993, Biological Evaluation of Medical Devices) medical devices such as the sensors described herein can be categorized into three groups based on implant duration: (1) "Limited" (<24 hours), (2) "Prolonged" (24 hours-30 days), and (3) "Permanent" (>30 days). In some embodiments of the invention, the design of the peroxide sensor of the invention allows for a "Permanent" implantation according to this categorization, i.e. >30 days. In related embodiments of the invention, the highly stable design of the peroxide sensor of the invention allows for an implanted sensor to continue to function in this regard for 2, 3, 4, 5, 6 or 12 or more months.

In general, the analyte sensor apparatus structure comprises a base layer and a conductive layer disposed upon the base layer (e.g. a porous matrix) and functions as one or more electrodes. For example, the conductive layer can include a working electrode, a reference electrode and/or a counter electrode. These electrodes can be spaced in proximity, or alternatively are spaced distally, according to the specific design. The sensor apparatus design is such that certain electrodes (e.g. the working electrode) can be exposed to the solution containing the analyte to be sensed (e.g. via an aperture) in the sensor apparatus. The sensor apparatus design is such that certain electrodes (e.g. the reference electrode) are not exposed to the solution containing the analyte to be sensed in the sensor apparatus.

One embodiment of the invention is a composition for use in biosensors. Such compositions are typically designed to be implantable within a mammal and comprise a porous matrix having a surface coated with an immobilized enzyme, for example glucose oxidase, glucose dehydrogenase, lactate oxidase, hexokinase or lactate dehydrogenase. Typically the porous matrix coated with an immobilized enzyme is capable of acting as an electrode in an electrochemical sensor. Optionally the electrode in the electrochemical sensor consumes hydrogen peroxide.

The matrices used in various embodiments of the biosensors of the invention can be generated from a variety of materials and can be adapted to a variety of compositional configurations. In some embodiments of the invention, the matrix is porous and comprises a ceramic material and/or a metal and/or a macroporous polymer. Optionally the porous matrix comprises a lattice of particles. Typically the particles are spherical. In typical embodiments of the invention, porous matrix has a surface area that is at least 2, 4, 6, 8, 10, 12, 14, 16 or 18 times the surface area of a non-porous matrix of same dimensions. In certain embodiments of the invention, the porous matrix is at least 1, 10, 100, or 1000 microns thick. In certain embodiments of the invention, the porosity range of the porous matrix is optionally about 5-99.9% and typically is about 40-99%. The porosity of these matrices can be measured by one of the protocols typically used in the art such as mercury or gas porosimetry, size-exclusion chromatography using marker molecules of various sizes and molecular weights (e.g. acetone, various globular proteins of a defined size, blue dextran), and cyclic voltammetry.

Typically, the analyte sensor apparatus includes an analyte sensing layer disposed on a conductive layer of the sensor, typically covering a portion or all of the working electrode. This analyte sensing layer detectably alters the electrical current at the working electrode in the conductive layer in the presence of an analyte to be sensed. As disclosed herein, this analyte sensing layer typically includes an enzyme or antibody molecule or the like that reacts with the analyte of interest in a manner that changes the concentrations of a molecule that can modulate the current at the working electrode (see e.g. oxygen and/or hydrogen peroxide as shown in the reaction scheme of FIG. 1). Illustrative analyte sensing layers comprise an enzyme such as glucose oxidase (e.g. for use in glucose sensors) or lactate oxidase (e.g. for use in lactate sensors). In some embodiments of the invention, the analyte sensing layer is disposed upon a porous metallic and/or ceramic and/or polymeric matrix with this combination of elements functioning as an electrode in the sensor.

Typically, the analyte-sensing layer further comprises a carrier protein in a substantially fixed ratio with the analyte sensing compound (e.g. the enzyme) and the analyte sensing compound and the carrier protein are distributed in a substantially uniform manner throughout the analyte sensing layer. Typically the analyte sensing layer is very thin, for example, less than 1, 0.5, 0.25 or 0.1 microns in thickness. While not being bound by a specific scientific theory, it is believed that sensors having such thin analyte sensing layers have surprisingly enhanced characteristics as compared to the thicker layers that are typically generated by electrodeposition because electrodeposition produces 3-5 micron thick enzyme layers in which only a fraction of the reactive enzyme within the coating layer is able to access the analyte to be sensed. Such thicker glucose oxidase pellets that are produced by electrodeposition protocols are further observed to have a poor mechanical stability (e.g. a tendency to crack) and further take a longer time to prepare for actual use, typically taking weeks of testing before it is ready for implantation. As these problems are not observed with the thin layered enzyme coatings described herein, these thin coatings are typical embodiments of the invention.

In sensors utilizing glucose oxidase for example, the thick coatings produced by electrodeposition may hinder the ability of hydrogen peroxide generated at the reactive interface of the 3-5 micron thick enzyme layer to contact the sensor surface and thereby generate a signal. In addition, hydrogen peroxide that is unable to reach a sensor surface due to such thick coatings can diffuse away from the sensor into the environment in which the sensor is placed, thereby decreasing the sensitivity and/or biocompatibility of such sensors. Moreover, while not being bound by a specific scientific theory, it is believed that sensors having such thin analyte sensing layers have unexpectedly advantageous properties that result from the fact that processes such as spin coating, or the like, allow for a precise control over the enzyme coating's ratio of glucose oxidase to albumin (which is used as a carrier protein to stabilize the glucose oxidase in the enzyme layer). Specifically, because glucose oxidase and albumin have different isoelectric points, electrodeposition processes may result in a surface coating in which an optimally determined ratio of enzyme to carrier protein is detrimentally altered in the electrodeposition process, and further wherein the glucose oxidase and the carrier protein are not distributed in a substantially uniform manner throughout the disposed enzyme layer. In addition, sensors having such thin analyte sensing layers have unexpectedly faster response times. While not being bound by a specific scientific theory, it is believed that these surprising and advantageous properties result from the observation that thin enzyme layers allow better access to the working electrode surface and may allow a greater proportion of the molecules that modulate current at the electrode to access the electrode surface. In this context, in certain sensor embodiments of the invention, an alteration in current in response to exposure to the analyte present in the body of the mammal can be detected via an amperometer within 15, 10, 5 or 2 minutes of the analyte contacting the analyte sensor.

Optionally, the analyte sensing layer has a protein layer disposed thereon and which is typically between this analyte sensing layer and the analyte modulating layer. A protein within the protein layer is an albumin selected from the group consisting of bovine serum albumin and human serum albumin. Typically this protein is crosslinked. Without being bound by a specific scientific theory, it is believed that this separate protein layer enhances sensor function and provides surprising functional benefits by acting as a sort of capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme such as GOx from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Typically, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer. This adhesion promoting layer typically comprises a silane compound such as γ-aminopropyltrimethoxysilane which is selected for its ability to promote optimized adhesion between the various sensor layers and functions to stabilize the sensor. Interestingly, sensors having such a silane containing adhesion promoting layers exhibit unexpected properties including an enhanced overall stability. In addition, silane containing adhesion promoting layers provide a number of advantageous characteristics in addition to an ability to enhancing sensor stability, and can, for example, play a beneficial role in interference rejection as well as in controlling the mass transfer of one or more desired analytes.

In certain embodiments of the invention, the adhesion promoting layer further comprises one or more compounds that can also be present in an adjacent layer such as the polydimethyl siloxane (PDMS) compounds that serves to limit the diffusion of analytes such as glucose through the analyte modulating layer. The addition of PDMS to the AP layer for example can be advantageous in contexts where it diminishes the possibility of holes or gaps occurring in the AP layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serve to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) comprising a polymer such as polydimethyl siloxane or the like. In certain embodiments of the invention, the analyte modulating layer comprises a hydrophilic comb-copolymer having a central chain and a plurality of side chains coupled to the central chain, wherein at least one side chain comprises a silicone moiety.

Typically the analyte modulating layer further comprises one or more cover layers which are typically electrically insulating protective layers disposed on at least a portion of the sensor apparatus (e.g. covering the analyte modulating layer). Acceptable polymer coatings for use as the insulating protective cover layer can include, but are not limited to, non-toxic biocompatible polymers such as silicone compounds, polyimides, biocompatible solder masks, epoxy acrylate copolymers, or the like. An illustrative cover layer comprises spun on silicone. Typically the cover layer further includes an aperture that exposes at least a portion of a sensor layer (e.g. analyte modulating layer) to a solution comprising the analyte to be sensed.

The analyte sensors described herein can be polarized cathodically to detect, for example, changes in current at the working cathode that result from the changes in oxygen concentration proximal to the working cathode that occur as glucose interacts with glucose oxidase as shown in FIG. 1. Alternatively, the analyte sensors described herein can be polarized anodically to detect for example, changes in current at the working anode that result from the changes in hydrogen peroxide concentration proximal to the working anode that occur as glucose interacts with glucose oxidase as shown in FIG. 1. In typical embodiments of the invention, the current at the working electrode(s) is compared to the current at a reference electrode(s) (a control), with the differences between these measurements providing a value that can then be correlated to the concentration of the analyte being measured. Analyte sensor designs that obtain a current value by obtaining a measurement from a comparison of the currents at these dual electrodes are commonly termed, for example, dual oxygen sensors.

In some embodiments of the invention, the analyte sensor apparatus is designed to function via anodic polarization such that the alteration in current is detected at the anodic working electrode in the conductive layer of the analyte sensor apparatus. Structural design features that can be associated with anodic polarization include designing an appropriate sensor configuration comprising a working electrode which is an anode, a counter electrode which is a cathode and a reference electrode, and then selectively disposing the appropriate analyte sensing layer on the appropriate portion of the surface of the anode within this design configuration. Optionally this anodic polarization structural design includes anodes, cathodes and/or working electrodes having different sized surface areas. For example, this structural design includes features where the working electrode (anode) and/or the coated surface of the working electrode is larger than the counter electrode (cathode) and/or the coated surface of the counter electrode. In this context, the alteration in current that can be detected at the anodic working electrode is then correlated with the concentration of the analyte. In certain illustrative examples of this embodiment of the invention, the working electrode is measuring and utilizing hydrogen peroxide in the oxidation reaction (see e.g. FIG. 1), hydrogen peroxide that is produced by an enzyme such as glucose oxidase or lactate oxidase upon reaction with glucose or lactate respectively. Such embodiments of the invention relating to electrochemical glucose and/or lactate sensors having such hydrogen peroxide recycling capabilities are particularly interesting because the recycling of this molecule reduces the amount of hydrogen peroxide that can escape from the sensor into the environment in which it is placed. In this context, implantable sensors that are designed to reduce the release of tissue irritants such as hydrogen peroxide will have improved biocompatibility profiles. Moreover as it is observed that hydrogen peroxide can react with enzymes such as glucose oxidase and compromise their biological function, such sensors are desired due to their avoidance of this phenomena. Optionally, the analyte modulating layer (e.g. a glucose limiting layer) can include compositions that serve to inhibit the diffusion of hydrogen peroxide out into the environment in which the sensor is placed. Consequently, such embodiments of the invention improve the biocompatibility of sensors that incorporate enzymes that produce hydrogen peroxide by incorporating hydrogen peroxide recycling elements disclosed herein.

Certain embodiments of the analyte sensors of the invention that comprise a base layer, a conductive layer, an analyte sensing layer, an optional protein layer, an adhesion promoting layer, an analyte modulating layer and a cover layer exhibit a number of unexpected properties. For example, in sensors that are structured to function via anodic polarization versus those structured to function via cathodic polarization, differences in the electrochemical reactions in the analyte sensing layer as well as at the electrode surface generate and/or consume different chemical entities, thereby altering the chemical environment in which the various sensor elements function in different polarities. In this context the sensor structure disclosed herein provides a surprisingly versatile device that is shown to function with an unexpected degree of stability under a variety of different chemical and/or electrochemical conditions.

In certain embodiments of the invention disclosed herein (e.g., those having hydrogen peroxide recycling capabilities) the sensor layer has a plurality of electrodes including a working electrode (e.g. an anode) and a counter electrode (e.g. a cathode), both of which are coated with an analyte sensing layer comprising an enzyme such as glucose oxidase or lactate oxidase. Such sensor designs have surprising properties including an enhanced sensitivity. Without being bound by a specific theory, these properties may result from the enhanced oxidation of hydrogen peroxide at the surface of a working or a counter electrode which produces additional oxygen that can be utilized in the glucose sensing reaction (see, e.g., FIG. 1). Therefore this recycling effect may reduce the oxygen dependent limitations of certain sensor embodiments disclosed herein. Moreover, this design may result in a sensor having a working electrode that can readily reduce available hydrogen peroxide and consequently have a lower electrode potential. Sensors designed to function with lower electrode potentials are typical embodiments of the invention because high electrode potentials in sensors of this type can result in a gas producing hydrolysis reaction which can destabilize the sensors (due to the disruption of sensor layers from gas bubbles produced by hydrolysis reactions). In addition, in sensor embodiments designed so that the counter electrode is coated with a very thin layer of an analyte sensing layer comprising an enzyme such as glucose oxidase or lactate oxidase, the hydrogen peroxide generated in the enzymatic reaction is very close to the reactive surface of the counter electrode. This can increase the overall efficiency of the sensor in a manner that allows for the production of compact sensor designs which include for example, counter electrodes with smaller reactive surfaces.

A specific illustrative example of an analyte sensor apparatus for implantation within a mammal is a peroxide sensor of the following design. A first layer of the peroxide sensor apparatus is a base layer, typically made from a ceramic such as alumina. A subsequent layer disposed upon the base layer is a conductive layer including a plurality of electrodes including an anodic working electrode and a reference electrode. A subsequent layer disposed on the conductive layer is an analyte sensing layer that includes crosslinked glucose oxidase which senses glucose and consequently generates hydrogen peroxide as shown in FIG. 1. In the presence of this hydrogen peroxide, the anodic working electrode experiences a measurable increase in current as the hydrogen peroxide generated contacts this anode in the conductive layer and is oxidized. The reference electrode serves as a control and is physically isolated from the working electrode and the hydrogen peroxide generated according to the reaction shown in FIG. 1. This analyte sensing layer is typically less than 1, 0.5, 0.25 or 0.1 microns in thickness and comprises a mixture of crosslinked human serum albumin in a substantially fixed ratio with the crosslinked glucose oxidase, with the glucose oxidase and the human serum albumin being distributed in a substantially uniform manner throughout the sensor layer. A subsequent layer disposed on the sensor layer is a protein layer comprising crosslinked human serum albumin. A subsequent layer disposed on the protein layer is an adhesion promoting layer which promotes the adhesion between the analyte sensing layer and/or the protein layer and an analyte modulating layer which is disposed upon these layers. This adhesion promoting layer comprises a silane composition. A subsequent layer disposed on the adhesion promoting layer is the analyte modulating layer in the form of a hydrophilic glucose limiting membrane comprising PDMS which modulates the diffusion of glucose therethrough. In certain embodiments of the invention, the analyte modulating layer comprises a hydrophilic comb-copolymer having a central chain and a plurality of side chains coupled to the central chain, wherein at least one side chain comprises a silicone moiety. A subsequent layer is a cover layer, typically composed of silicone, which is disposed on at least a portion of the analyte modulating layer, wherein the cover layer further includes an aperture that exposes at least a portion of the analyte modulating layer to the external glucose containing environment so that the glucose can access the analyte sensing layer on the working electrode. This peroxide sensor apparatus functions via anodic polarization such that the hydrogen peroxide signal that is generated by glucose diffusing through the analyte modulating layer and then reacts with the glucose oxidase in the analyte sensing layer creates a detectable change in the current at the anodic working electrode in the conductive layer of the sensor that can be measured by an amperometer. This change in the current at the anodic working electrode can then be correlated with the concentration of glucose in the external environment. Consequently, a sensor of this design can act as a peroxide based glucose sensor.

E. Permutations of Analyte Sensor Apparatus and Elements

As noted above, the invention disclosed herein includes a number of embodiments including sensors having very thin enzyme coatings. Such embodiments of the invention allow artisans to generate a variety of permutations of the analyte sensor apparatus disclosed herein. As noted above, illustrative general embodiments of the sensor disclosed herein include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 2 illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

An illustrative embodiment of the invention is shown in FIG. 2. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In an illustrative embodiment as shown in FIG. 2 the analyte sensing layer comprises a conductive layer 104 which is disposed on insulating base layer 102. Typically the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, non-toxic biocompatible polymers such as polyimide, biocompatible solder masks, epoxy acrylate copolymers, or the like. Further, these coatings can be photo-imagable to facilitate photolithographic forming of apertures 108 through to the conductive layer 104. In certain embodiments of the invention, an analyte sensing layer is disposed upon a porous metallic and/or ceramic and/or polymeric matrix with this combination of elements functioning as an electrode in the sensor.

In the sensors of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photoresist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize a separate reference element not formed on the sensor. The exposed electrodes and/or contact pads can also undergo secondary processing through the apertures 108, such as additional plating processing, to prepare the surfaces and/or strengthen the conductive regions.

An analyte sensing layer 110 is typically disposed on one or more of the exposed electrodes of the conductive layer 104 through the apertures 108. Typically, the analyte sensing layer 110 is a sensor chemistry layer and most typically an enzyme layer. Typically, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The sensor chemistry layer 110 can be applied over portions of the conductive layer or over the entire region of the conductive layer. Typically the sensor chemistry layer 110 is disposed on portions of a working electrode and a counter electrode that comprise a conductive layer. Some methods for generating the thin sensor chemistry layer 110 include spin coating processes, dip and dry processes, low shear spraying processes, ink-jet printing processes, silk screen processes and the like. Most typically the thin sensor chemistry layer 110 is applied using a spin coating process.

The analyte sensing layer 110 is typically coated with one or more coating layers. In some embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art. In certain embodiments of the invention, the analyte modulating layer comprises a hydrophilic comb-copolymer having a central chain and a plurality of side chains coupled to the central chain, wherein at least one side chain comprises a silicone moiety.

In some embodiments of the invention, a coating layer is a glucose limiting membrane layer 112 which is disposed above the sensor chemistry layer 110 to regulate glucose contact with the sensor chemistry layer 110. In some embodiments of the invention, an adhesion promoter layer 114 is disposed between the membrane layer 112 and the sensor chemistry layer 110 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the sensor chemistry layer 110 can be sufficiently crosslinked or otherwise prepared to allow the membrane layer 112 to be disposed in direct contact with the sensor chemistry layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more typically substantially all of a surface of the sensor, and that is capable of interacting with one or more analytes, such as chemical compounds, cells and fragments thereof, etc., in the environment in which the sensor is disposed. Non-limiting examples of functional coating layers include sensor chemistry layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including an UV-absorbing polymer. In some embodiments, the UV-absorbing polymer is a polyurethane, a polyurea or a polyurethane/polyurea copolymer. More typically, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; U.S. Pat. No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming an UV-absorbing polymer layer above or below a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensors of the present invention are particularly designed for use as subcutaneous or transcutaneous glucose sensors for monitoring blood glucose levels in a diabetic patient. Typically each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

The sensors of the invention can have any desired configuration, for example planar or cylindrical. The base layer 102 can be self-supportive, such as a rigid polymeric layer, or non-self supportive, such as a flexible film. The latter embodiment is desirable in that it permits continuous manufacture of sensors using, for example, a roll of a polymeric film which is continuously unwound and upon which sensor elements and coating layers are continuously applied.

A general embodiment of the invention is a sensor designed for implantation within a body that comprises a base layer, an analyte sensing layer disposed upon the base layer which includes a plurality of sensor elements, an enzyme layer (typically less than 2 microns in thickness) disposed upon the analyte sensing layer which coats all of the plurality of sensing elements on the conductive layer, and one or more coating layers. Typically the enzyme layer comprises glucose oxidase; typically in a substantially fixed ratio with a carrier protein. In a specific embodiment, the glucose oxidase and the carrier protein are distributed in a substantially uniform manner throughout the disposed enzyme layer. Typically the carrier protein comprises albumin, typically in an amount of about 5% by weight. As used herein, "albumin" refers to those albumin proteins typically used by artisans to stabilize polypeptide compositions such as human serum albumin, bovine serum albumin and the like. In some embodiments of the invention, a coating layer is an analyte contacting layer which is disposed on the sensor so as to regulate the amount of analyte that can contact the enzyme layer. In further embodiments, the sensor includes an adhesion promoter layer disposed between the enzyme layer and the analyte contacting layer; and, the enzyme layer is less than 1, 0.5, 0.25 or 0.1 microns in thickness.

Embodiments of the invention include a design where an analyte sensing layer is disposed upon a porous metallic and/or ceramic and/or polymeric matrix with this combination of elements functioning as an electrode in the sensor. A related embodiment of the invention is an electrochemical analyte sensor which includes a base layer, a conductive layer disposed upon the base layer that includes at least one working electrode and at least one counter electrode, an analyte sensing layer disposed upon the conductive layer, wherein the analyte sensing layer is less than 2 microns in thickness; and an analyte modulating layer that regulates the amount of analyte that contacts the enzyme layer, typically by limiting the amount of analyte that can diffuse through the layer and contact the analyte sensing layer. In certain embodiments of the invention, the analyte modulating layer comprises a hydrophilic comb-copolymer having a central chain and a plurality of side chains coupled to the central chain, wherein at least one side chain comprises a silicone moiety. In an optional embodiment of the invention, the working electrode and/or the coated surface of the working electrode is larger than counter electrode and/or the coated surface of the counter electrode. In some embodiments, the enzyme layer comprises glucose oxidase stabilized by coating it on the working electrode and the counter electrode in combination with a carrier protein in a fixed ratio. In one embodiment, this glucose oxidase enzyme layer substantially covers the conductive layer. Embodiments where the glucose oxidase enzyme layer is disposed in a uniform coating over the whole conductive layer are typical because they may avoid problems associated with sensors having multiple different coatings on a single layer such as the selective delamination of different coatings having different material properties. Typically, the sensor includes an adhesion promoting layer disposed between the enzyme layer and the analyte modulating layer.

A related embodiment of the invention is an electrochemical analyte sensor which includes a base layer, a conductive layer disposed upon the base layer that includes at least one working electrode, at least one reference electrode and at least one counter electrode, an enzyme layer disposed upon the conductive layer, and an analyte modulating cover layer that regulates the amount of analyte that contacts the enzyme layer. In some embodiments, the enzyme layer is less than 2 microns in thickness and is coated on at least a portion of the working electrode, the reference electrode and the counter electrode. In an illustrative embodiment, the enzyme layer substantially covers the working electrode, the reference electrode and the counter electrode. Optionally, the enzyme layer comprises glucose oxidase in combination with a carrier protein (e.g. albumin) in a fixed ratio. Typically, the sensor includes an adhesion promoting layer disposed between the enzyme layer and the analyte modulating layer.

Yet another embodiment of the invention comprises a glucose sensor for implantation within a body which includes a base layer, a conductive layer disposed upon the base layer, an analyte sensing layer comprising glucose oxidase disposed upon the conductive layer, wherein the glucose oxidase is stabilized by combining it with albumin in a defined ratio and further wherein the glucose oxidase and the albumin are distributed in a substantially uniform manner throughout the disposed layer, and a glucose limiting layer that regulates the amount of glucose that diffuses through the glucose limiting layer and contacts the glucose oxidase layer. In some embodiments, the conductive layer includes a plurality of sensor elements including at least one working electrode and at least one counter electrode.

F. Analyte Sensor Apparatus Configurations

In a clinical setting, accurate and relatively fast determinations of analytes such as glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference. As noted below, embodiments of the invention disclosed herein have a wider range of geometrical configurations (e.g. planar) than existing sensors in the art. In addition, certain embodiments of the invention include one or more of the sensors disclosed herein coupled to another apparatus such as a medication infusion pump.

FIG. 2 provides a diagrammatic view of a typical analyte sensor configuration of the current invention. Certain sensor configurations are of a relatively flat "ribbon" type configuration that can be made with the analyte sensor apparatus. Such "ribbon" type configurations illustrate an advantage of the sensors disclosed herein that arises due to the spin coating of sensing enzymes such as glucose oxidase, a manufacturing step that produces extremely thin enzyme coatings that allow for the design and production of highly flexible sensor geometries. Such thin enzyme coated sensors provide further advantages such as allowing for a smaller sensor area while maintaining sensor sensitivity, a highly desirable feature for implantable devices (e.g. smaller devices are easier to implant). Consequently, sensor embodiments of the invention that utilize very thin analyte sensing layers that can be formed by processes such as spin coating can have a wider range of geometrical configurations (e.g. planar) than those sensors that utilize enzyme layers formed via processes such as electrodeposition.

Certain sensor configurations include multiple conductive elements such as multiple working, counter and reference electrodes. Advantages of such configurations include increased surface area which provides for greater sensor sensitivity. For example, one sensor configuration introduces a third working sensor. One obvious advantage of such a configuration is signal averaging of three sensors which increases sensor accuracy. Other advantages include the ability to measure multiple analytes. In particular, analyte sensor configurations that include electrodes in this arrangement (e.g. multiple working, counter and reference electrodes) can be incorporated into multiple analyte sensors. The measurement of multiple analytes such as oxygen, hydrogen peroxide, glucose, lactate, potassium, calcium, and any other physiologically relevant substance/analyte provides a number of advantages, for example the ability of such sensors to provide a linear response as well as ease in calibration and/or recalibration.

An exemplary multiple sensor device comprises a single device having a first sensor which is polarized cathodically and designed to measure the changes in oxygen concentration that occur at the working electrode (a cathode) as a result of glucose interacting with glucose oxidase; and a second sensor which is polarized anodically and designed to measure changes in hydrogen peroxide concentration that occurs at the working electrode (an anode) as a result of glucose coming form the external environment and interacting with glucose oxidase. As is known in the art, in such designs, the first oxygen sensor will typically experience a decrease in current at the working electrode as oxygen contacts the sensor while the second hydrogen peroxide sensor will typically experience an increase in current at the working electrode as the hydrogen peroxide generated as shown in FIG. 1 contacts the sensor. In addition, as is known in the art, an observation of the change in current that occurs at the working electrodes as compared to the reference electrodes in the respective sensor systems correlates to the change in concentration of the oxygen and hydrogen peroxide molecules which can then be correlated to the concentration of the glucose in the external environment (e.g. the body of the mammal).

The analyte sensors of the invention can be coupled with other medical devices such as medication infusion pumps. In an illustrative variation of this scheme, replaceable analyte sensors of the invention can be coupled with other medical devices such as medication infusion pumps, for example by the use of a port couple to the medical device (e.g. a subcutaneous port with a locking electrical connection).

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al., "In Vivo Measurement of Subcutaneous Glucose Concentrations with an Enzymatic Glucose Sensor and a Wick Method," Klin. Wochenschr. 67:491-495 (1989); and Pickup, et al., "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

B. Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as deltin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including chemical vapor deposition, physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a sensor chemistry enzyme layer can then be disposed on the sensing layer by electrochemical deposition or a method other than electrochemical deposition such a spin coating, followed by vapor crosslinking, for example with a dialdehyde (glutaraldehyde) or a carbodi-imide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Subsequent to treatment of the sensor elements, one or more additional functional coatings or cover layers can then be applied by any one of a wide variety of methods known in the art, such as spraying, dipping, etc. Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as exact the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt %. Among the copolymers listed above, the dimethylsiloxane-bisphenol A carbonate copolymer which comprises 50-55 wt % of the nonsiloxane component is typical. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane nonsiloxane copolymer, where compatible.

In some embodiments of the invention, the sensor is made by methods which apply an analyte modulating layer that comprises a hydrophilic membrane coating which can regulate the amount of analyte that can contact the enzyme of the sensor layer. For example, the cover layer that is added to the glucose sensors of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic comb-copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate the contact between the hydrogen peroxide molecules and the electrode sensing elements.

In some embodiments of the methods of invention, an adhesion promoter layer is disposed between a cover layer (e.g. an analyte modulating membrane layer) and a sensor chemistry layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrirnethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

Like certain other coating layers of the sensor, the adhesion promoter layer can be subjected to one or more suitable radiation and/or chemical and/or heat curing steps as are known in the art. In alternative embodiments, the enzyme layer can be sufficiently crosslinked or otherwise prepared to allow the membrane cover layer to be disposed in direct contact with the sensor chemistry layer in the absence of an adhesion promoter layer.

An illustrative embodiment of the invention is a method of making a sensor by providing a base layer, forming a sensor layer on the base layer, spin coating an enzyme layer on the sensor layer and then forming an analyte contacting layer (e.g. an analyte modulating layer such as a glucose limiting membrane) on the sensor, wherein the analyte contacting layer regulates the amount of analyte that can contact the enzyme layer. In some methods, the enzyme layer is vapor crosslinked on the sensor layer. In a typical embodiment of the invention, the sensor layer is formed to include at least one working electrode and at least one counter electrode. In certain embodiments, the enzyme layer is formed on at least a portion of the working electrode and at least a portion of the counter electrode. Typically, the enzyme layer that is formed on the sensor layer is less than 2, 1, 0.5, 0.25 or 0.1 microns in thickness. Typically, the enzyme layer comprises one or more enzymes such as glucose oxidase, glucose dehydrogenase, lactate oxidase, hexokinase or lactate dehydrogenase and/or like enzymes. In a specific method, the enzyme layer comprises glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, the adhesion promoter layer is subjected to a curing process prior to the formation of the analyte contacting layer.

A related embodiment of the invention is a method of making a glucose sensor by providing a base layer, forming a sensor layer on the base layer that includes at least one working electrode and at least one counter electrode, forming a glucose oxidase layer on the sensor layer by a spin coating process (a layer which is typically stabilized by combining the glucose oxidase with albumin in a fixed ratio), wherein the glucose oxidase layer coats at least a portion of the working electrode and at least a portion of the counter electrode, and then forming a glucose limiting layer on the glucose sensor so as to regulate the amount of glucose that can contact the glucose oxidase layer. In such processes, the glucose oxidase layer that is formed on the sensor layer is typically less than 2, 1, 0.5, 0.25 or 0.1 microns in thickness. Typically, the glucose oxidase coating is vapor crosslinked on the sensor layer. Optionally, the glucose oxidase coating covers the entire sensor layer. In certain embodiments of the invention, an adhesion promoter layer is disposed between the glucose oxidase layer and the analyte contacting layer. In certain embodiments of the invention, the analyte sensor further comprises one or more cover layers which are typically electrically insulating protective layers (see, e.g. element 106 in FIG. 2). Typically, such cover layers are disposed on at least a portion of the analyte modulating layer.

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. The functional coating layer(s) can be applied either before or after other sensor components are removed from the supporting substrate (e.g., by cutting).

III. Methods for Using Analyte Sensor Apparatus of the Invention

A related embodiment of the invention is a method of sensing an analyte within the body of a mammal, the method comprising implanting an analyte sensor embodiment disclosed herein in to the mammal and then sensing an alteration in current at the working electrode and correlating the alteration in current with the presence of the analyte, so that the analyte is sensed. Typically the analyte sensor is polarized anodically such that the working electrode where the alteration in current is sensed is an anode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds a porous matrix that is coated with a layer of an enzyme such as glucose oxidase. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

Various publication citations are referenced throughout the specification. In addition, certain text from related art is reproduced herein to more clearly delineate the various embodiments of the invention. The disclosures of all citations in the specification are expressly incorporated herein by reference.

EXAMPLES

The following examples are given to aid in understanding the invention, but it is to be understood that the invention is not limited to the particular materials or procedures of examples. All materials used in the examples were obtained from commercial sources.

Example 1

Synthesis of Silicone-Based Comb-Copolymer 9.6 g polydimethyl siloxane monomethacrylate (Mw=1000), 4.08 g methoxy poly(ethylene oxide) monomethacrylate (Mw=1000), 10.32 g methyl methacrylate, 50 mg 2,2'-azobisisobutyronitrile and 60 ml ethoxy ethyl acetate were added into a 200 mL round bottom flask containing a magnetic stirring bar. All chemicals were mixed together by Stirring for 20 min.

Made two-time freeze—vacuum—thaw-nitrogen for mixture to remove all oxygen in the round bottle flask.

The flask was placed into one oil bath. The solution was then heated to 75° C. After 16-24 h, the bottle was removed from the oil batch and allowed to cool down to room temperature.

The polymer solution was precipitated into 1000 ml of DI water and filtered out, then dissolved in 100 ml of THF again, and precipitated into 1000 ml $H_2O$.

The solid polymer was filtered out and dried at 70° C. until constant weight.

Example 2

Synthesis of Silicone-Based Comb-Copolymer 7.2 g polydimethyl siloxane monomethacrylate (Mw=1000), 7.2 g vinyl pyrolidone, 9.6 g methyl methacrylate, 50 mg 2,2'-azobisisobutyronitrile and 60 ml THF were added into a 200 mL round bottom flask containing a magnetic stirring bar. All chemical were mixed together by Stirring for 20 min.

Made two-time freeze—vacuum—thaw-nitrogen for mixture to remove all oxygen in the round bottle flask.

The flask was placed into one oil bath. The solution was then heated to 75° C. After 16-24 h, the bottle was removed from the oil batch and allowed to cool down to room temperature.

The polymer solution was precipitated into 1000 ml of DI water, dissolved in 100 ml of THF again and precipitated into 1000 ml $H_2O$.

The solid polymer was filtered out and dried at 70° C. until constant weight.

More representative silicone based comb-copolymers prepared by the above procedure are listed in Table 1.

Example 3

Figure 7:
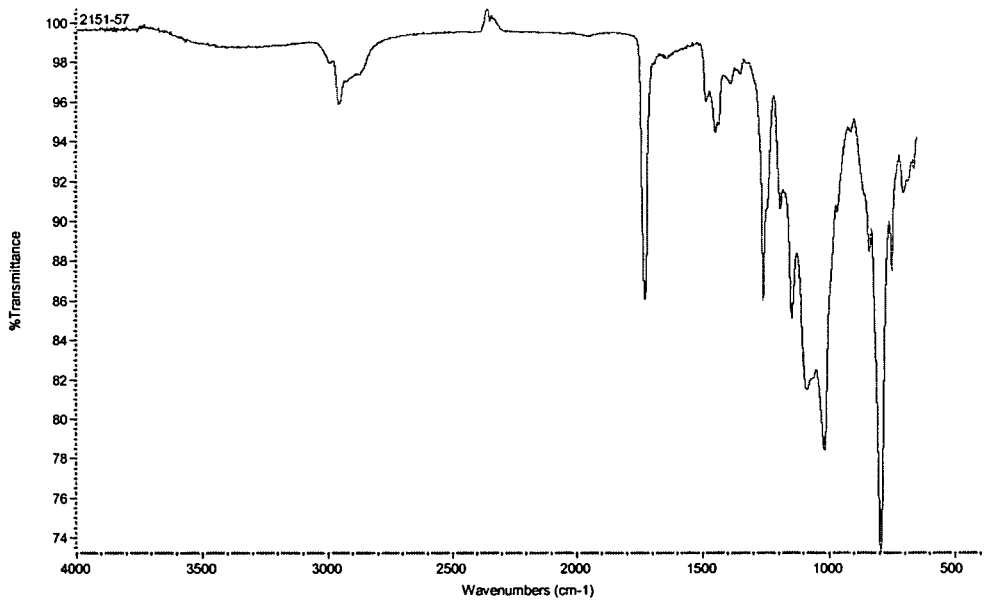
FIG. 7 shows an infrared spectrum of an exemplary comb-copolymer in the present invention.

Characterization of Silicone-Based Comb-Copolymers a). Molecular weights of comb-copolymers were determined by Gel Permeation Chromatography (Waters, Inc) using THF/acetic acid (95:5 v/v) as mobile phase. Monodisperse Polystyrene standards were used for calibration. All data are showed in Table 2.

b). Infrared spectra of comb-copolymers were obtained using Nicolet Nexus 670 FT-IR. FIG. 7 shows the spectrum of sample #5 listed in Table 1, exhibiting the expected absorbance band ($cm^{-1}$).

c). Water uptake was determined gravimetrically at room temperature on films which were less then 0.5 mm thick. After evaporation of casting solvent, films were dried to constant weight at 50° C. in vacuum oven, weighted, immersed in deionzed water for 24 h, removed and blotted with filter paper, and weighted. Percent water uptake was determined from the formula:

% uptake=$[(W_w-W_d)/W_d]\times100$

Where $W_w$ is the weight of the swollen film and $W_d$ is the weight of the dry film. The results are shown in Table 2.

d). Diffusion constants were measured in a standard diffusion cell (Crown Glass Co. Inc.) maintained at 37° C. using Fick's relationship:

J=D dC/dx

Where J is total flux, D is the diffusion constant, and dC/dx is the concentration gradient across the membrane.

Glucose diffusion constant ($D_G$) was determined by securing the membrane with two rubber gasket between the two halves of a diffusion cell maintained at 37° C. One side was filled with 2400 mg/dL glucose in phosphate buffered saline (PBS, 0.15M NaCl, 0.05M phosphate, PH=7.4), the other side was filled with phosphate buffered saline. The concentration of glucose in each half of the cell was measured at appropriate intervals using a YSI glucose analyzer. The curve of concentration vs. time was plotted and the diffusion constant was calculated. Results are shown in Table 2.

Oxygen diffusion constant ($D_o$) was determined using the same diffusion cell. Each side of the cell was filled with phosphate buffered saline. One side was saturated with high purity $O_2$, the other side was saturated with high purity $N_2$. Two calibrated oxygen electrodes were placed in two cells and oxygen concentration from both cells were recorded as a function of time. The curve of oxygen concentration vs. time was plotted and the constant was calculated. Curve generally had correlation coefficients ($R^2$) of greater than 0.99. All data are set forth in Table 2.

Example 4

Figure 8:
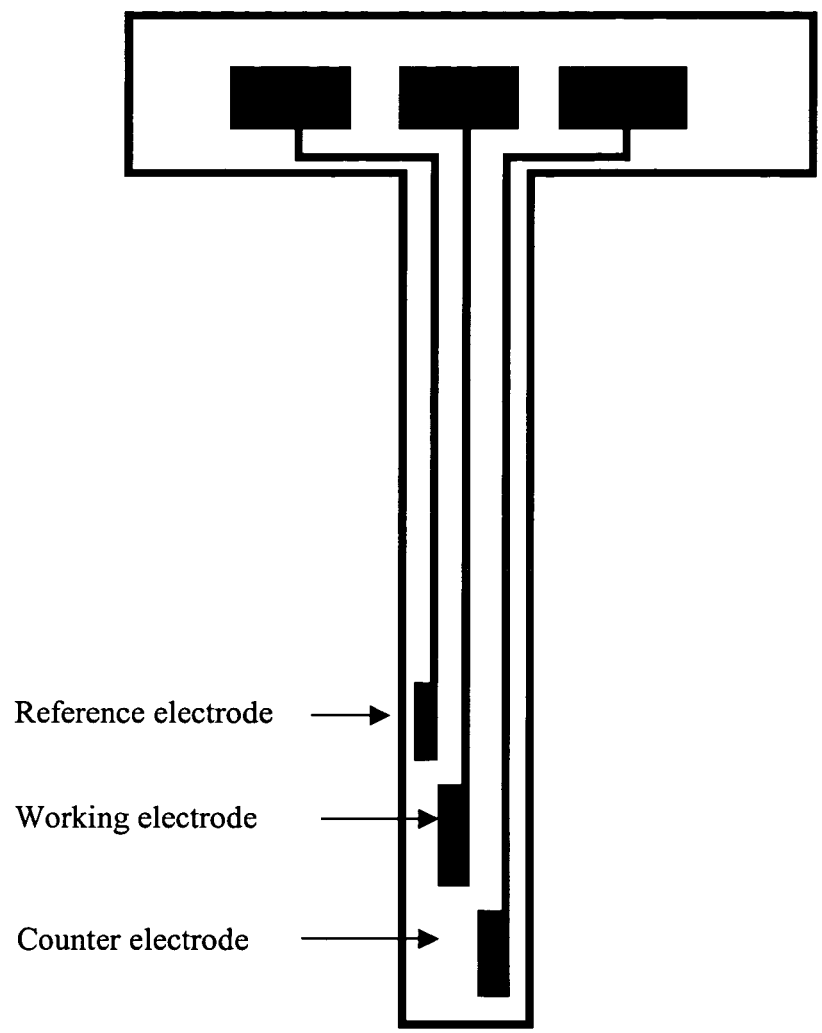
FIG. 8 is a schematic top view of an exemplary glucose sensor having electrodes covered with an exemplary polymer of the present invention.
Figure 9:
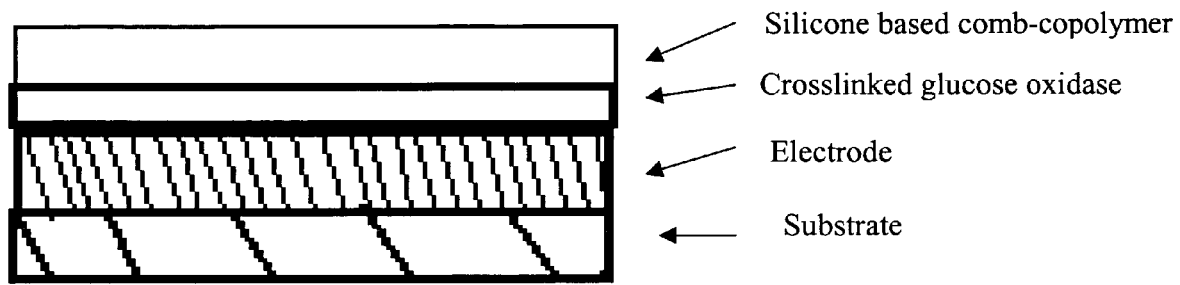
FIG. 9 is a sectional side view of a working electrode covered with layers of enzyme and the polymer composition of the present invention.
Figure 10:
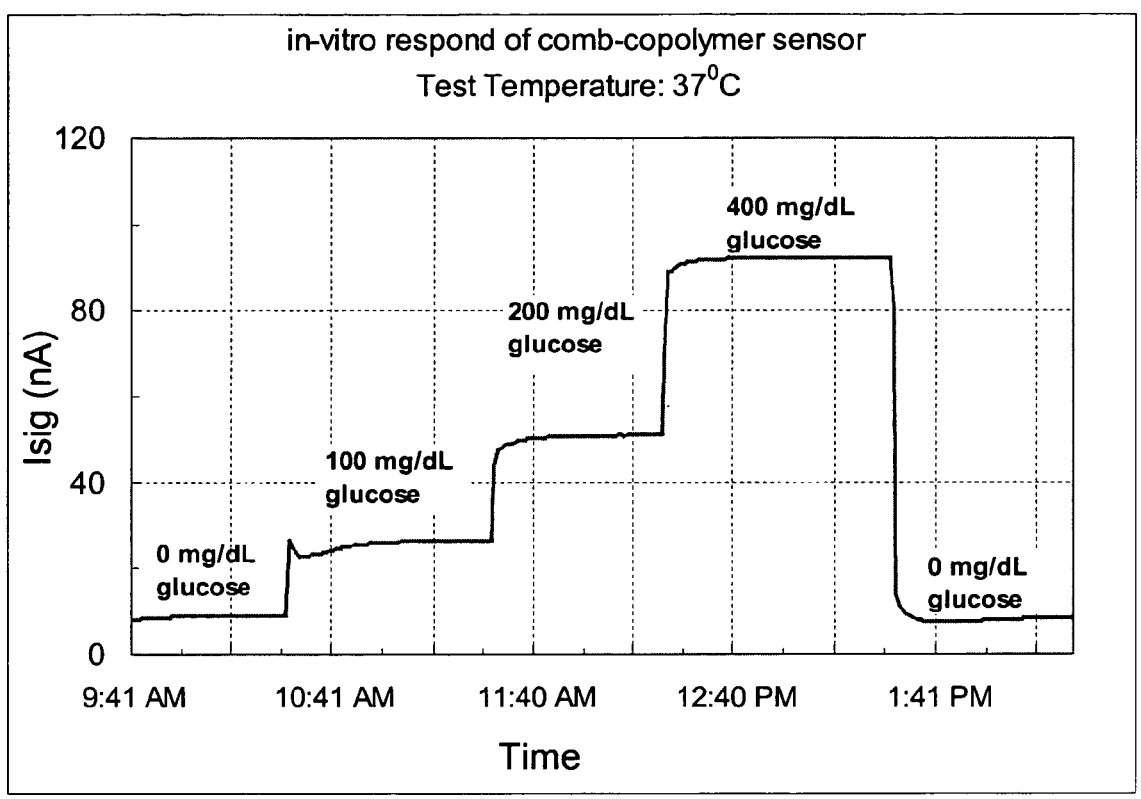
FIG. 10 is a graph showing in-vitro performance of comb-copolymer sensor in different glucose solutions
Figure 11:
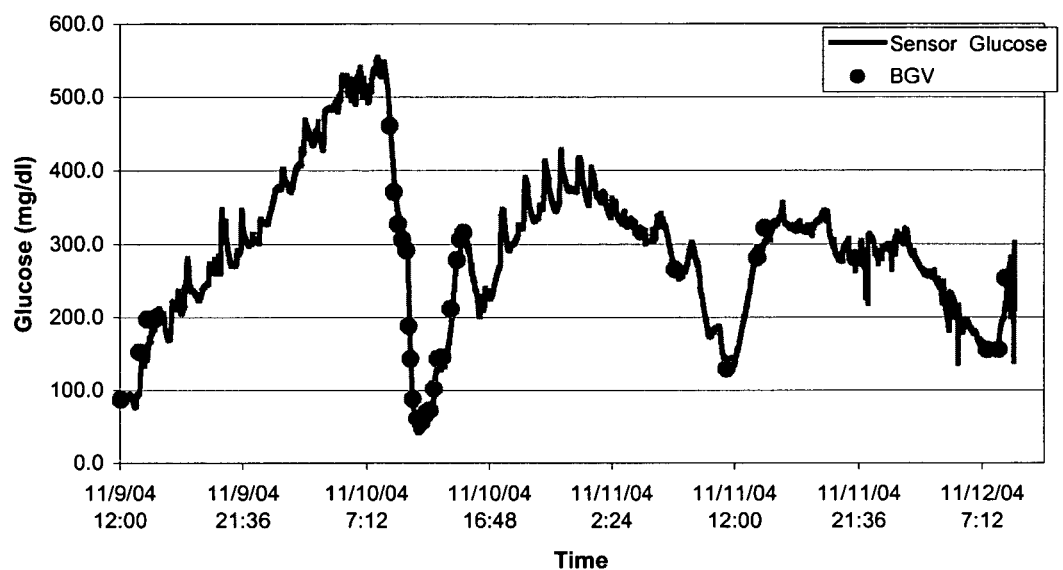
FIG. 11 is a graph showing in-vivo performance of comb-copolymer sensor in a canine model.

Sensor Preparation Using Silicone-Based Comb-Copolymer and Sensor Performance in In-Vitro and In-Vivo Testing a). The silicone-based comb-copolymer was evaluated using a prototype glucose sensor illustrated in FIG. 8 and FIG. 9. According to FIGS. 8 and 9, a sensor was constructed having a reference electrode, a working electrode, and a counter electrode deposited on a polyimide sheet. As shown in FIG. 9, the electrodes were covered with a layer of cross-linked glucose oxidase and then coated with a layer of silicone-based comb-copolymer by spray coating of comb-copolymer solution in THF.

b). Glucose response in in-vitro testing is shown in FIG. 10 (comb-copolymer #5 in Table 1 is used in this example). The response of the electrode system was close to linear relationship over the physiological glucose range. The sensor didn't show oxygen effect even at very low oxygen level (2%).

c). In-vivo testing result (FIG. 11, made from comb-copolymer #5 in Table 1) shows sensor with new comb-copolymer tracks blood glucose level very well in Canine.

Tables

TABLE 1

SYNTHESIS OF COMB-COPOLYMERS

| # | PDMS-MA (wt %) | PEO-MA (wt %) | VP (wt %) | MMA (wt %) |
|---|---|---|---|---|
| 1 (2213-37-1) | 30% | 25% | 0% | 45% |
| 2 (2213-47-1) | 30% | 25% | 0% | 50% |
| 3 (2213-54-1) | 30% | 18% | 0% | 52% |
| 4 (2213-56-2) | 35% | 18% | 0% | 47% |
| 5 (2151-57) | 35% | 17% | 0% | 48% |
| 6 | 40% | 17% | 0% | 43% |
| 7 (2151-58) | 35% | 16% | 0% | 49% |
| 8 (2213-47-2) | 30% | 15% | 0% | 55% |
| 9 (2213-54-2) | 50% | 20% | 0% | 30% |
| 10 (2213-56-1) | 40% | 18% | 0% | 42% |
| 11 (2213-59-2) | 30% | 0% | 30% | 40% |

PDMA-MA: polydimethyl siloxane monomethacrylate (Mw is about 1000 g/mol)
PEO-MA: poly(ethylene oxide) methyl ether methacrylate (Mw is about 1000 g/mol)
VP: n-vinyl pyrrolidone
MMA: methyl methacrylate

TABLE 2

CHARACTERIZATION OF COMB-COPOLYMERS

| # | Mw (kg/mol) | Glucose diffusion constant (cm²/s) | $O_2$ diffusion constant (cm²/s) | Water Uptake (%) |
|---|---|---|---|---|
| 1 (2213-37-1) | 161 | $140 \times 10^{-9}$ | $1.30 \times 10^{-5}$ | 40 |
| 2 (2213-47-1) | 167 | $22 \times 10^{-9}$ | $1.10 \times 10^{-5}$ | 20 |
| 3 (2213-54-1) | 196 | $17 \times 10^{-9}$ | $1.03 \times 10^{-5}$ | 21 |
| 4 (2213-56-2) | 139 | $17 \times 10^{-9}$ | $1.38 \times 10^{-5}$ | 19 |
| 5 (2151-57) | 138 | $7.8 \times 10^{-9}$ | $1.42 \times 10^{-5}$ | 22 |
| 6 | — | — | — | — |
| 7 (2151-58) | 186 | $3.7 \times 10^{-9}$ | $1.32 \times 10^{-5}$ | 17 |
| 8 (2213-47-2) | 167 | $2.3 \times 10^{-9}$ | $0.95 \times 10^{-5}$ | 14 |
| 9 (2213-54-2) | 180 | — | — | 30 |
| 10 (2213-56-1) | 145 | $18 \times 10^{-9}$ | $1.73 \times 10^{-5}$ | 27 |
| 11 (2213-59-2) | 185 | — | — | 3 |

The invention claimed is:

1. An analyte sensor apparatus for implantation within a mammal, the analyte sensor apparatus comprising:
   a base layer;
   a conductive layer disposed upon the base layer wherein the conductive layer includes a working electrode;
   an analyte sensing layer disposed on the conductive layer, wherein the analyte sensing layer detectably alters the electrical current at the working electrode in the conductive layer in the presence of an analyte; and
   an analyte modulating layer disposed on the analyte sensing layer,
   wherein:
   the analyte modulating layer modulates the diffusion of the analyte therethrough;
   the analyte modulating layer comprising a hydrophilic comb-copolymer having a central chain and a plurality of side chains coupled to the central chain;
   the hydrophilic comb-copolymer comprises a polydimethyl siloxane monomethacrylate, methyl methacrylate; and methoxy poly(ethylene oxide)monomethacrylate comb-copolymer;
   the analyte modulating layer exhibits a glucose diffusion coefficient of between $2.3 \times 10^{-9}$ cm²/s and $140 \times 10^{-9}$ cm²/s; and
   the analyte modulating layer comprises:
   30-50 wt % polydimethyl siloxane monomethacrylate;
   30-55 wt % methyl methacrylate; and
   15-25 wt % methoxy poly(ethylene oxide)monomethacrylate,
   such that the comb-copolymer exhibits a molecular weight from 139 kg/mol to 196 kg/mol.

2. The analyte sensor apparatus of claim 1, wherein analyte modulating layer exhibits a water uptake between 20% and 40%.

3. The analyte sensor apparatus of claim 2, wherein the analyte modulating layer has a oxygen diffusion coefficient ($D_{oxygen}$) to glucose diffusion coefficient ($D_{glucose}$) ratio ($D_{oxygen}/D_{glucose}$) of from 5 to 2000.

4. An analyte sensor apparatus for implantation within a mammal, the analyte sensor apparatus comprising:
   a base layer;
   a conductive layer disposed upon the base layer wherein the conductive layer includes a working electrode;
   an analyte sensing layer disposed on the conductive layer, wherein the analyte sensing layer detectably alters the electrical current at the working electrode in the conductive layer in the presence of an analyte; and
   an analyte modulating layer disposed on the analyte sensing layer,
   wherein:
   the analyte modulating layer modulates the diffusion of the analyte therethrough; the analyte modulating layer comprising a hydrophilic comb-copolymer having a central chain and a plurality of side chains coupled to the central chain; and
   the analyte modulating layer exhibits:
   (a) a glucose diffusion coefficient of between $2.3 \times 10^{-9}$ cm²/s and $140 \times 10^{-9}$ cm²/s;
   (b) a oxygen diffusion coefficient ($D_{oxygen}$) to glucose diffusion coefficient ($D_{glucose}$) ratio ($D_{oxygen}/D_{glucose}$) of from 5 to 2000; and a water uptake between 20% and 40%; and
   (c) the analyte modulating layer comprises:
   30-50 wt % polydimethyl siloxane monomethacrylate;
   30-55 wt % methyl methacrylate; and
   15-25 wt % methoxy poly(ethylene oxide)monomethacrylate,
   such that the comb-copolymer exhibits a molecular weight from 139 kg/mol to 196 kg/mol.

5. The analyte sensor apparatus of claim 4, wherein at least one side chain is hydrophilic.

6. The analyte sensor apparatus of claim 4, wherein at least one side chain is hydrophobic.

7. The analyte sensor apparatus of claim 4, wherein the central chain is hydrophilic.

* * * * *